United States Patent [19]

Cohen et al.

[11] 4,011,211

[45] Mar. 8, 1977

[54] STEROID TOTAL SYNTHESIS PROCESS UTILIZING ASYMMETRIC INDUCTION

[75] Inventors: Noal Cohen, Montclair; Gabriel Saucy, Essex Fells, both of N.J.

[73] Assignee: Hoffmann-La Roche Inc., Nutley, N.J.

[22] Filed: Sept. 24, 1975

[21] Appl. No.: 616,239

Related U.S. Application Data

[62] Division of Ser. No. 406,980, Oct. 16, 1973, Pat. No. 3,932,519, which is a division of Ser. No. 100,372, Dec. 21, 1970, abandoned.

[52] U.S. Cl. .................. 260/239.55 R; 260/397.4; 260/397.5; 260/345.9; 260/476 C; 260/488 CD; 260/590 FA
[51] Int. Cl.² .......................................... C07J 17/00
[58] Field of Search ............... 260/239.55 R, 397.4, 260/397.5, 345.9, 590, 488 CD, 476 C

[56] References Cited

OTHER PUBLICATIONS

Douglas et al., J. Chem. Soc. (London) 1963 pp. 5072–5094.

*Primary Examiner*—Gerald A. Schwartz
*Attorney, Agent, or Firm*—Samuel L. Welt; George M. Gould; Raymond R. Wittekind

[57] ABSTRACT

A multi-step, stereospecific total synthesis of steroids is disclosed. The starting materials for this process are the relatively inexpensive and readily available m-alkoxy aceto-phenones. The process is suitable for the preparation of racemic or optically active, medicinally valuable steroids, particularly A-ring aromatic steroids. This process features an early optical resolution and a unique asymmetric induction which insures the correct stereochemistry of the final steroidal product.

1 Claim, No Drawings

STEROID TOTAL SYNTHESIS PROCESS UTILIZING ASYMMETRIC INDUCTION

This is a division, of application Ser. No. 406,980 filed Oct. 16, 1973, now U.S. Pat. No. 3,932,519 issued Jan. 13, 1976 which is a division of application Ser. No. 100,372, filed Dec. 21, 1970, now abandoned.

BRIEF DESCRIPTION OF THE INVENTION

The present invention relates to a multi-step, stereospecific total synthesis of racemic or optically active, medicinally valuable steroids which makes use of a novel asymmetric induction for the control of the stereochemistry. The synthesis is particularly adapted for the production of A-ring aromatic steroids.

One aspect of the present invention involves the preparation of racemic or optically active compounds of the following formula:

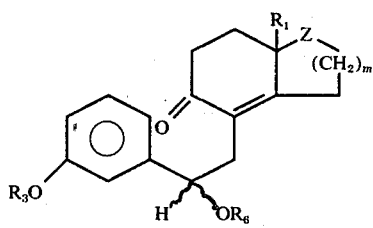

wherein $R_1$ is a primary alkyl group of from 1 to 5 carbon atoms; $R_3$ is a cycloalkyl group, or a primary alkyl group of from 1 to 8 carbon atoms; $R_6$ is hydrogen, lower acyl or aroyl; Z is carbonyl or a group of the formula

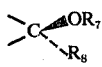

where $R_7$ is hydrogen, lower acyl, lower alkyl, aryl lower alkyl or tetrahydropyran-2-yl and $R_8$ is hydrogen or lower aliphatic hydrocarbyl; and $m$ is 1 or 2.

As used throughout the specification and appended claims, the term hydrocarbyl group denotes a monovalent substituent consisting solely of carbon and hydrogen and having from 1 to 20 carbon atoms; the term aliphatic with reference to hydrocarbyl groups, denotes groups containing no aromatic unsaturation, but which can be saturated or unsaturated, i.e., an alkyl, alkenyl or alkynyl group; the term alkyl group denotes a saturated hydrocarbyl group with a straight or branched chain having from 1 to 20 carbon atoms unless otherwise indicated; the term cycloalkyl group denotes a saturated hydrocarbyl group containing a 3 to 8 membered ring having its valence bond from a ring carbon; the term alkenyl denotes a straight or branched chain hydrocarbyl group having at least 1 olefinic bond and containing from 1 to 20 carbon atoms; the term alkynyl group denotes a straight or branched chain hydrocarbyl group containing at least 1 acetylenic bond having from 1 to 20 carbon atoms; the term primary alkyl group denotes an alkyl group having its valence from a carbon bound to at least 2 hydrogens; the term aliphatic hydrocarbylene group denotes a straight or branched chain divalent substituent consisting solely of carbon and hydrogen containing no aromatic unsaturation having its valence bonds from different carbons; the term aryl-ene group denotes an aromatic divalent substituent having its valence bonds from the aromatic ring; the term acyl group denotes a group consisting of the residue of a hydrocarbyl monocarboxylic acid having from 1 to 18 carbon atoms formed by removal of the hydroxyl portion of the carboxyl group; and the term lower, as applied to any of the foregoing groups, denotes a group having a carbon skeleton containing up to and including 8 carbon atoms, such as methyl, ethyl, butyl, tertiary butyl, hexyl, 2-ethylhexyl, vinyl, butenyl, hexynyl, ethynyl, ethylene, methylene, formyl, acetyl, 2-phenylethyl and the like.

In the formulae presented herein, the various substituents on cyclic compounds are joined to the cyclic nucleus by one of three notations, a solid line (—) indicating a substituent which is in the β-orientation (i.e., above the plane of the paper), a dotted line (·····) indicating a substituent which is in the α-orientation (below the plane of the paper) or a wavy line (∼) indicating a substituent which may be either in the α- or β-orientation. The position of $R_1$ has generally been arbitrarily indicated as the β-orientation, although the products obtained in the examples are all racemic compounds unless otherwise specified.

Preferred compounds of formula I are those wherein $R_1$ is n-alkyl, especially methyl and ethyl; $R_3$ is methyl; $m$ is 1 and Z is a carbonyl or a β-hydroxy methylene group.

A further aspect of the present invention concerns processes useful in the preparation of racemic or optically active forms of compounds of formula Ia

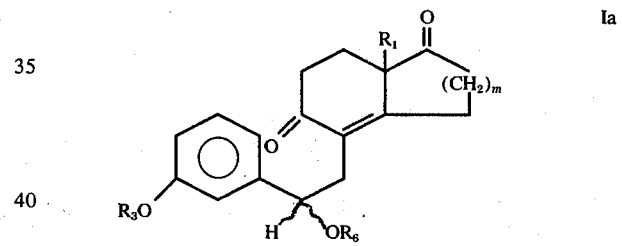

where $R_1$, $R_3$, $R_6$ and $m$ are as above, utilizing commercially available and relatively inexpensive starting materials. For example, a preferred synthetic route for the preparation of compounds of formula Ia, utilizes a 3-(3'-alkoxy-benzoyl)propionitrile or the corresponding carboxylic acid. These starting materials are generally known but if a specific material is not known, it may be prepared in an analogous manner as the known compounds from the corresponding m-alkoxy-acetophenone.

Processes for the preparation of the subgeneric compounds

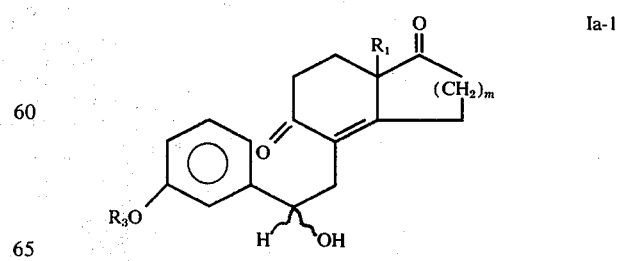

where $R_1$, $R_3$ and $m$ are as above, are summarized in the following Reaction Scheme.

REACTION SCHEME I

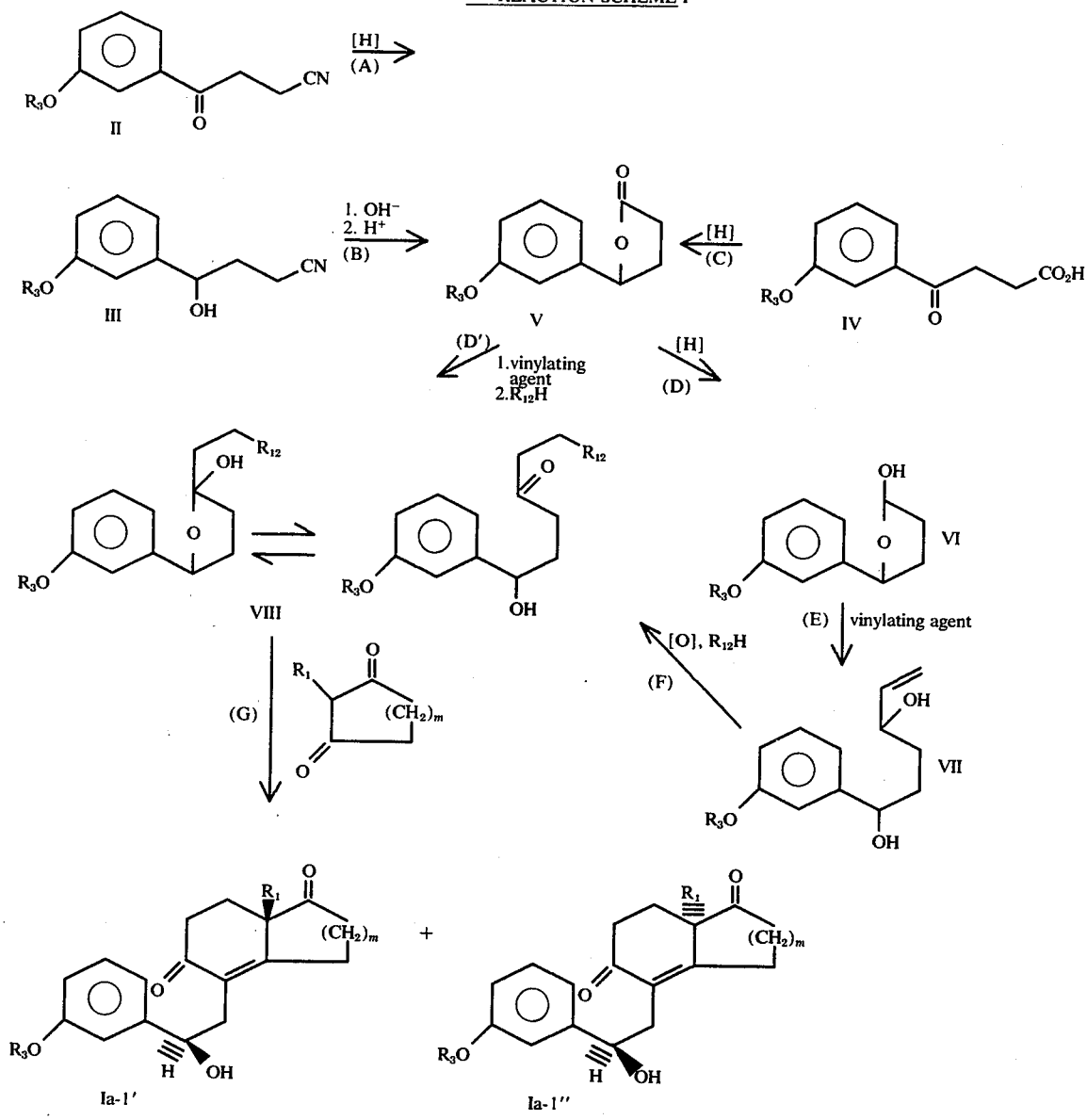

wherein
R$_1$, R$_3$, R$_6$ and m are as above and

R$_{12}$ is chloro; bromo; iodo; hydroxy; lower alkoxy; lower hydrocarbylamino or di(lower hydrocarbyl)amino.

CHART FOR REACTION SCHEME I

| Step | Reagents Operable | Preferred | Solvent Operable | Preferred | Conditions Operable | Preferred | Remarks |
|---|---|---|---|---|---|---|---|
| A | Alkali metal borohydrides, e.g., sodium borohydride; alkoxy substituted alkali metal borohydrides, e.g. trimethoxy sodium borohydride; alkoxy substituted complex metal hydrides, e.g., tri-t-butoxy lithium aluminum hydride | Sodium borohydride<br><br><br><br><br><br><br>pyridine and di- | A non-ketonic organic solvent selected from the group consisting of lower alkanols, e.g., methanol; water miscible ethers, e.g., tetrahydrofuran;<br><br>methylformamide; or a mixture of water and one or more of the above. | Ethanol | −20° to boiling point of solvent | −10° to 20° | |
| B | a. dilute aqueous alkali metal hydroxide e.g., sodium hydroxide or potassium hydroxide | a. dilute aqueous sodium hydroxide | No additional solvents are necessary but a water-miscible organic ether, e.g. tetrahydrofuran or | No additional solvent | a. −40° to boiling point of solvent | a. boiling point of solvent | The base treatment in part a can be done |

-continued
CHART FOR REACTION SCHEME I

|   |   |   |   |   |   |   |   |
|---|---|---|---|---|---|---|---|
|   | b. dilute aqueous mineral acid, e.g., hydrochloric acid; dilute aqueous organic sulfonic acid, e.g., p-toluene sulfonic acid. | b. dilute aqueous hydrochloric acid | dioxane can be employed. |   | b. 0° to 30° | b. room temperature | either upon the 3-hydroxy compound or its ester or half ester. |
| C | a. same as for Step A | a. sodium boro hydride | A non-ketonic organic solvent selected from the group consisting of lower alkanols, e.g.; methanol water miscible ethers e.g.; tetrahydrofuran pyridine and dimethylformamide; or a mixture of water and one or more of the above | Water containing an alkali metal hydroxide, e.g. sodium hydroxide | a. −10° to +50° | a. 20° to 30° |   |
|   | b. dilute aqueous mineral acid, e.g. hydrochloric acid; dilute aqueous organic sulfonic acid, e.g., p-toluene sulfonic acid | b. dilute aqueous hydrochloric acid |   |   | b. 20° to 60° | b. 40° to 50° |   |
| D | dialkyl aluminum hydride e.g., diisobutyl-aluminum hydride | diisobutyl-aluminum-hydride | aliphatic hydrocarbons, e.g., hexane; aromatic hydrocarbons, e.g., benzene or toluene | Toluene | −100 to −50° | −70° |   |
| E | Vinyl magnesium halides e.g., vinyl magnesium chloride; vinyl alkali metal, e.g., vinyl lithium | Vinyl magnesium chloride | Ethers, e.g., diethyl ether, tetrahydrofuran | Tetrahydrofuran | −20 to +50° | 0° to 30° |   |
| F | Manganesedioxide and a reagent selected from the group consisting of hydrogen halides, e.g., hydrogen chloride; lower alkanols, e.g., methanol; water; lower hydrocarbyl amines, e.g., ethylamine; di(lower hydrocarbyl) amines, e.g., diethylamine | Manganesedioxide and diethylamine | Aliphatic hydrocarbons, e.g., hexane; aromatic hydrocarbons, e.g., benzene; organic ethers, e.g., tetrahydrofuran. | Benzene | −20° to +40° | 0° to 20° |   |
| D' | a. vinyl magnesium halides e.g., vinyl magnesium chloride; vinyl alkali metals, e.g., vinyl lithium | a. vinyl magnesium chloride | a. ethers, e.g., diethyl ether, tetrahydrofuran | a. tetrahydrofuran | a. −40 to −100° | a. −50° to −60° |   |
|   | b. a reagent selected from the group consisting of hydrogen halides, e.g., hydrogen chloride; lower alkanols, e.g., methanol; water; lower hydrocarbyl amines, e.g., ethylamine; di(lower hydrocarbyl)amines, e.g., diethylamine | b. diethylamine | b. aliphatic hydrocarbons, e.g., hexane; aromatic hydrocarbons, e.g., benzene; organic ethers, e.g., ethyl ether | b. ethyl ether | b. 0° to 40° | b. 0° to 20° |   |
| G | 2-alkyl-cyclopentan-1,3-diones, e.g., 2-methyl-cyclopentan-1,3-dione; 2-alkyl-cyclohexan-1,3-diones, e.g., 2-methyl-cyclohexan-1,3-dione | 2-methyl cyclopentan-1,3-dione; 2-ethyl cyclopentan-1,3-dione | Aromatic hydrocarbons, e.g., toluene; organic ethers, e.g. tetrahydrofuran; dimethylformamide; dimethylsulfoxide | Toluene | 20° to 150° | 80° to 120° | An acidic catalyst can be used, preferably a lower alkanoic acid, e.g., acetic acid. |

In Step A the ketonitrile, compound II, is converted to the hydroxy nitrile, compound III, by reduction with a complex metal hydride reducing agent, for example, sodium borohydride.

If one wishes to produce optically active steroids having the natural d-configuration, it is especially desirable to resolve compound III to afford the desired optical antipode, formula IIIa,

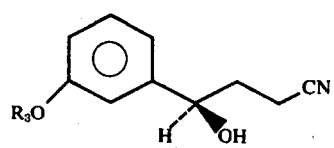

IIIa where $R_3$ is as above, or a suitable derivative for the conversion to lactone V.

Such an optical resolution may be accomplished in a number of ways. One procedure for resolving a racemic compound of formula III is to react it with an optically active compound such as a carboxylic acid, a carboxylic acid halide or anhydride, an isocyanate, and so forth, to afford a mixture of diastereomeric derivatives, separating the diastereomers by methods known per se such as, for example, crystallization or chromatography, and hydrolyzing the desired diastereomer to afford the desired enantiomer of compound III, or the corresponding lactone V. Examples of suitable reagents for the preparation of the diastereomeric mixtures described above are tartranilic acid, menthyl isocyanate, d- or 1-α-methylbenzylisocyanate, menthoxy acetyl chloride, 3β-acetoxy-Δ⁵-etiocholenic acid and so forth.

It is preferred, however, to resolve compounds of formula III by first converting them to a half ester of the formula

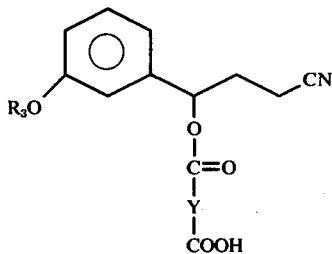

wherein $R_3$ is as above and Y is an aliphatic hydrocarbylene group having from 2 to 5 carbon atoms or an arylene group, with a suitable derivative of a dicarboxylic acid, $Y(COOH)_2$, and then resolving the half ester by converting it to a mixture of diastereomeric salts with an optically active amine.

Suitable dicarboxylic acids include succinic acid, glutaric acid, adipic acid, pimelic acid, maleic acid, fumaric acid, phthalic acid, terephthalic acid, naphthalene 2,3-dicarboxylic acid, and the like. The diastereomeric salts are separated by methods known per se, as described above, preferably by fractional crystallization, and the desired diastereomeric salt can be decomposed by treatment with strong acid, or strong base to afford either the desired enantiomer of the compound of formula III or, more preferably, the half ester derivative. It is convenient to use the anhydride of a dicarboxylic acid to prepare the half ester. Thus, for example, compound III can be reacted with succinic or phthalic anhydride in the presence of a base such as, for example, pyridine to afford the corresponding acid succinate or acid phthalate. It is especially preferred to resolve the acid phthalate. Suitable optically active bases that can be used for the resolution are, for example, α-methylbenzylamine, α-methylnaphthylamine, dehydroabietylamine, leucine, ephedrine, strychnine, cinchonine, quinine, amphetamine, morphine, menthylamine, and so forth. β-Methylbenzylamine is preferred. d-(+)-α-Methylbenzylamine is especially preferred, since the desired diastereomeric salt (i.e., the one which leads to steroids having the natural d-configuration) is the less soluble and is easily purified by recrystallization.

Suitable solvents for recrystallization of the mixture of diastereomeric salts are ketones, e.g., acetone; ethers, e.g., diisopropyl ether; lower alkanols, e.g., n-butanol and acetonitrile. Acetonitrile is especially preferred.

In Reaction Step B, racemic or optically active hydroxy nitrile III is hydrolyzed and cyclized to the lactone of formula V by treatment with aqueous base, followed by acidification. For the preparation of optically active V, it is convenient to utilize the half ester of the desired enantiomer of III without the necessity of first hydrolyzing it to the free alcohol.

The lactone V can also be prepared, as shown in Reaction Step C, by reduction of a keto acid of formula IV with a complex metal hydride reducing agent, such as for example, sodium borohydride, and subsequent acidification. In this reaction, however, one can prepare only racemic V. Therefore, it is necessary to utilize the nitrile sequence when optically active products are desired.

It should be pointed out at this time that the early resolution in the reaction sequence presents a number of advantages of the present process over those previously used for total synthesis of steroids. One advantage resides in the fact, that since the compound being resolved possesses only one chiral center, it can easily be racemized or converted to an achiral compound that can be recycled in the reaction process.

Thus, the unwanted optical isomer of compound III can be racemized by treatment by strong base since it possesses an acidic benzylic hydrogen atom at the chiral center. Alternatively, the unwanted antipode can be oxidized to compound II by standard oxidation techniques such as, for example, chromium trioxide or potassium permanganate oxidation, thus destroying the asymmetry, and the resulting achiral ketonitrile II can then be reutilized in the present process. Alternatively, the undesired antipode of lactone V can be converted to the desired antipode by methods known per se. In this manner, it is not necessary to discard half of the potential product as is necessary in many other resolution processes for the total synthesis of steroids.

Lactone V can be converted to lactol VI in Reaction Step D by reaction at reduced temperature with a metal hydride reducing reagent such as, for example, diisobutyl aluminum hydride.

In Step E, the lactol of formula VI is converted to the vinyl diol of formula VII by treatment with a vinylating agent.

In Reaction Step F, the allylic hydroxyl group of compound VII is selectively oxidized, in the presence of a benzylic hydroxyl group, by treatment with an oxidizing agent such as, for example, manganese dioxide, in the presence of a trapping agent, $R_{12}H$, where $R_{12}$ is as above. In such a manner, the addition product (compound VIII, shown in both open and closed forms) is obtained directly. This reaction most probably proceeds through the vinyl ketone intermediate

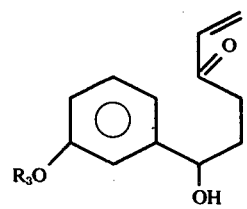

i where $R_3$ is as above.

In an alternate process, step D', the lactone V can be converted to compound VIII by vinylation and subsequent reaction of the intermediate vinyl ketone with $R_{12}H$.

If one utilizes a racemic lactone V or racemic vinyl diol VII in the preparation of compound VIII, as described above, using as $R_{12}H$, an optically active amine, the resulting mixture of diastereomeric Mannich bases of formula VIII can be separated to afford a pure diastereomer. The diastereomer having a 6-R stereochemistry is especially desired as it leads to steroids having the natural configuration. The separation and purification of the desired diastereomer can be done by methods known per se, such as recrystallization or chromatography. Suitable optically active amines are enantiomers of α-methylbenzylamine, α-methylnaphthylamine, dehydroabietylamine and so forth. It is particularly convenient to separate said diastereomeric Mannich bases as their acid addition salts with mineral acids, e.g., hydrochloric acid, or non-optically active organic acids, e.g., oxalic acid.

The condensation of compound VIII with a 2-alkyl cycloalkane 1,3-dione to afford compounds Ia-1' and Ia-1'' is one of the key features of the present process. It is in this condensation that specific stereochemical induction at one member of the critical C/D ring junction of the eventual steroidal product occurs. Thus, this invention is particularly advantageous in that it involves a unique asymmetric induction. The products of the condensation, i.e., the diketones of formula Ia-1' and Ia-1'', have two asymmetric centers at positions 2 and 7a(8a) respectively and, therefore, two racemates or four optical antipodes are possible. However, as a result of the condensation of this invention, when using a racemic starting material of formula VIII, mainly one of the two possible racemates is formed, Ia-1', i.e., the isomer where $R_1$ and the OH groups are cis. For synthesis of a racemic steroidal final product, both of the racemates can be used. When one starts with an optically active lactone V and carries it through the above reaction sequence, the optical antipode having the absolute configuration depicted by formula Ia-1' is mainly formed. The desired optical antipode Ia-1' can be obtained in high purity by, for example, recrystallization or chromatography of the crude reaction product.

The condensation reaction (Step G) proceeds very readily, one hour in refluxing toluene usually being sufficient, in contrast to the known cyclization [H. Smith, et al., J. Chem. Soc. 5072 (1963)] of triketones not having a benzylic hydroxyl group, which require seven days. Thus, unexpectedly the presence of the benzylic hydroxyl group in compounds of formula VIII greatly facilitates their conversion to the important intermediates of formula Ia.

It is particularly useful to esterify compounds of formula Ia-1' and Ia-1'' (i.e. the mixture obtained from the condensation reaction) to product suitable highly crystalline esters, $R_6'$ is lower acyl or aroyl.

A preferred ester derivative is the p-bromobenzoate. The esterification is accomplished in the normal manner, utilizing for example, a carboxylic acid halide or anhydride in the presence of a base such as pyridine.

The mixture of esters can be treated by standard techniques, such as recrystallization, to afford the desired ester Ia-2' in pure form. This purification is particularly desirable when one desires to prepare an optically active steroid, since all traces of the undesired component of the condensation mixture must be removed. As stated above, when synthesizing racemic steroids, both components may be carried through the reaction sequence without the need for separation.

If desired, after purification of the ester, the group $R_6'$ may be cleaved by methods known per se to afford back the pure compound of formula Ia-1'. However, it is especially convenient to utilize compounds of formula Ia-2' in further reaction processes without the need to first hydrolyze the ester group.

It has been found that when starting with lactone V having a 5-R absolute configuration there is eventually obtained, as the major product, the optical antipode of formula Ia-1' having the desired 7a(8a)-S stereoconfiguration. Thus, to prepare steroidal materials having the more desirable 13β-stereoconfiguration by the synthesis of this invention, one should start with the antipode of formula Ia-1' which is prepared starting with the 5-R antipode of compound V. In summary, the unique asymmetric induction concurrent to the condensation of this invention renders the obtention of a single optical antipode as an end-product more facile.

The compounds of subgenus Ia are readily converted to the corresponding 1β-alcohols and their esters and ethers as represented by the following formula

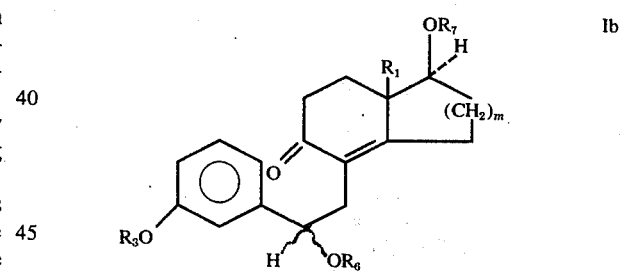

where $R_1$, $R_3$, $R_6$, $R_7$ and m are as above, by the sequence of reactions comprising reduction of the 1-ketone to the alcohol, and if desired, subsequent esterification or etherification.

The reduction can be effected by the use of a limited amount of a metal hydride reducing reagent such as an

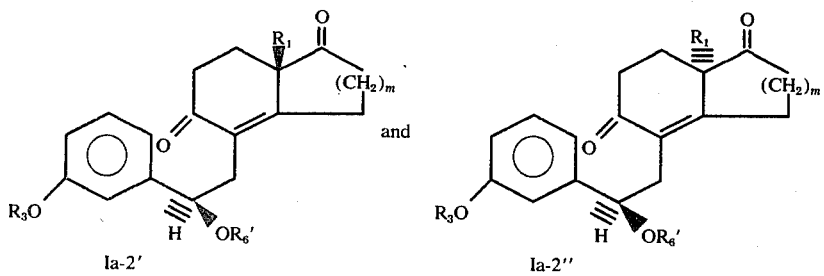

wherein
$R_1$, $R_3$ and m are as above and alkali metal borohydride, e.g., sodium borohydride; an alkoxy substituted alkali metal borohydride, e.g., trimethoxy sodium borohydride; or an alkoxy substituted complex metal hydride, e.g., lithium aluminum tri-t-butoxy hydride. Generally, one mole-equivalent of hydride is preferred. The reaction is effected in any suitable reaction medium, such as ethers, e.g., diethyl ether or tetrahydrofuran; water; a lower alkanol, e.g., methanol; N,N-di(lower alkyl)-lower alkanoyl amides, e.g., N,N-dimethylformamide; or aromatic amines, e.g., pyridine. The use of a hydrocarbon co-solvent, e.g., benzene, to solubilize the reactants is sometimes necessary. The remaining reaction conditions are not narrowly critical, although it is generally preferred to effect the reduction between about 0° C. and room temperature.

The free alcohol is recovered from the reaction mixture after acidification. The alcohol can be esterified in a known manner, for example, by base-catalyzed reaction with a carboxylic acid halide or carboxylic acid anhydride. Illustrative bases include sodium hydroxide, potassium hydroxide, an alkaline metal alkoxide, or an amine, especially a tertiary amine such as pyridine or picoline. Such reaction is conveniently carried out in an inert organic solvent, for example, benzene, at a temperature of about room temperature.

The alcohols can also be etherified in a known manner by acid catalyzed reaction with an olefin, e.g., isobutylene or 2,3-dihydropyran. Suitable acids include mineral acids, organic sulfonic acids and Lewis acids. The etherification is conveniently accomplished in an inert organic solvent at about room temperature. If a volatile olefin is employed, the reaction is conveniently carried out in a closed vessel. The diketones of subgenus Ia can be converted to their 1β-hydroxy-1α-hydrocarbyl derivatives and their 1β-esters and ethers represented by the following formula

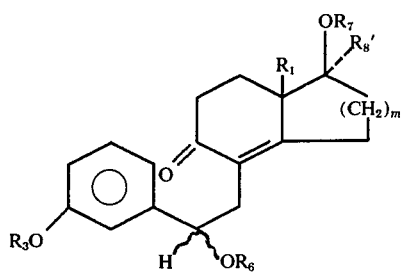

wherein
$R_1$, $R_3$, $R_6$, $R_7$ and $m$ are as above, and
$R_8'$ is lower aliphatic hydrocarbyl.

A suitable method involves first protecting the 5-ketone by use of a suitable protecting group known in the art such as for example a conventionally hydrolyzable ketal or enol ether, then reacting the 1-ketone of the protected compound with a hydrocarbyl magnesium halide such as methyl magnesium chloride or vinyl magnesium chloride or with a hydrocarbyl alkali metal compound such as methyl lithium, sodium acetylide, potassium acetylide, and the like. Finally, the protecting group is removed from the 5-position to afford a 1-hydroxy compound of formula Ic which may be optionally esterified or etherified at the 1-position. If $OR_6$ represents an ester group in compound Ia then said ester will by hydrolyzed during the above hydrocarbylation reaction. The resulting hydroxy group can be reesterified, if desired, by the standard procedure.

While it is within the scope of the present invention to introduce a 1α-alkyl, -alkenyl or -alkynyl group at this point or at any of the subsequent stages described below, it is not desirable to introduce an alkenyl or alkynyl group at any point prior to the formation of compound XII since said alkenyl or alkynyl group will necessarily be reduced to the corresponding alkyl group during subsequent hydrogenation processes. Thus, such groups would only serve as precursors of the corresponding alkyl groups.

As indicated above, the compounds of formula I are useful as intermediates for the preparation of various medicinally valuable steriod compounds. This is illustrated by the following Reaction Scheme:

REACTION SCHEME II

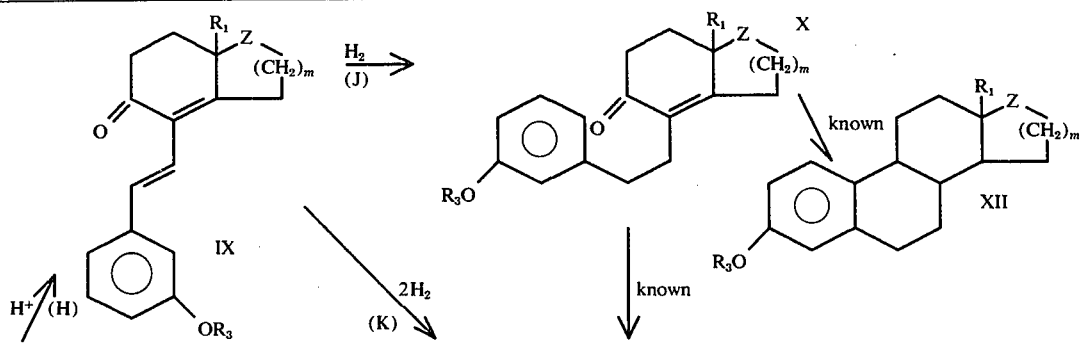

REACTION SCHEME II-continued

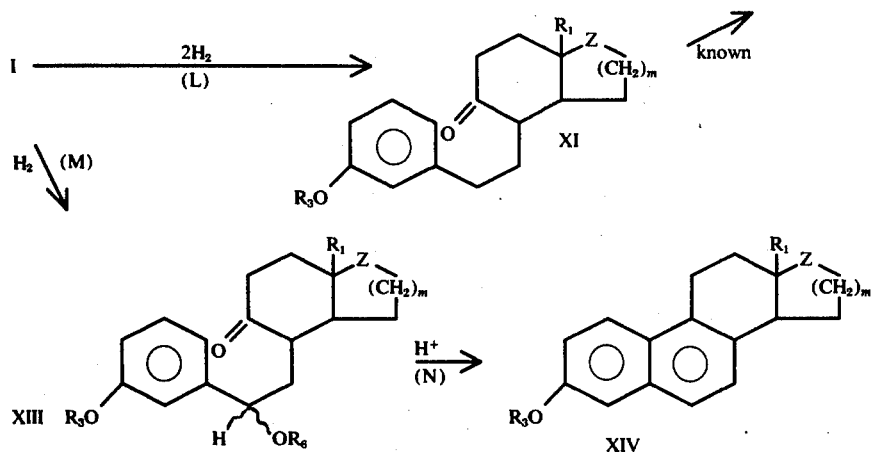

where $R_1$, $R_3$, $R_6$, Z and m are as above.

CHART FOR REACTION SCHEME II

| Step | Reagents Operable | Preferred | Solvent Operable | Preferred | Conditions Operable | Preferred | Remarks |
|---|---|---|---|---|---|---|---|
| H | Mineral acids, e.g. hydrochloric acid; organic sulfonic acids, e.g., p-toluene sulfonic acid; Lewis acids, e.g., boron-trifluoride. | p-toluene sulfonic acid | Aliphatic hydrocarbons, e.g., hexane; aromatic hydrocarbons, e.g., toluene; organic ethers, e.g., dioxane | Toluene | 50° to 150° | 80° to 120° | |
| J | Hydrogen and a metal catalyst e.g., palladium, platinum, rhodium, Raney nickel, either unsupported or on a suitable support. | Palladium on charcoal catalyst | Aliphatic hydrocarbons, e.g., hexane; aromatic hydrocarbons, e.g., toluene; organic ethers, e.g., tetrahydrofuran; lower alkanols, e.g., methanol | Toluene | 0° to 50°; 1 to 10 atmospheres | Room temperature; 1 atmosphere | The hydrogenation is terminated after the uptake of 1 mole-equivalent of hydrogen. |
| K | Same as in | Reaction | Step J. | Ethanol | Same as in Step J. | Reaction | The hydrogenation is continued until 2-mole-equivalents of hydrogen were taken up. |
| L | Hydrogen and a metal catalyst e.g., palladium, platinum, rhodium, Raney nickel, either unsupported or on a suitable support. | Palladium on charcoal catalyst | aliphatic hydrocarbons, e.g., hexane; aromatic hydrocarbons, e.g., toluene; organic ethers, e.g., tetrahydrofuran; lower alkanols, e.g., ethanol | Ethanol | 0° to 50°; 1 to 10 atmospheres | Room temperature; 1 atmosphere | The hydrogenation is continued until 2-mole-equivalents of hydrogen are taken up. |
| M | Hydrogen and a metal catalyst e.g., palladium, platinum, rhodium, Raney nickel, either unsupported or on a suitable support. | Palladium on barium sulfate catalyst | Aliphatic hydrocarbons, e.g., hexane; aromatic hydrocarbons, e.g., toluene; organic ethers, e.g., tetrahydrofuran; lower alkanols, e.g., methanol | Ethanol | 0° to 50°; 1 to 10 atmospheres | Room temperature; 1 atmosphere | The hydrogenation is terminated after 1-mole-equivalent of hydrogen has been taken up. |
| N | Polyphosphoric acid; hydrogen halides, e.g., hydrogen chloride; organic sulfonic acids, e.g., p-toluene sulfonic acid. | hydrogen chloride followed by p-toluenesulfonic acid. | aromatic hydrocarbons, e.g., benzene; organic ethers, e.g., tetrahydrofuran; lower alkanols, e.g., methanol | Benzene and methanol. | 50° to 150° | 70° to 100° | |

In Reaction Step H, compound I is reacted with a strong acid to eliminate the $OR_6$ group in the benzylic position and to afford the novel diene of structure IX. This diene most likely has the trans-geometry shown.

The styrene double bond of compound IX can be selectively hydrogenated if desired (Step J), to afford a compound of structure X. This can be done by stopping the hydrogenation after 1 mole equivalent of hydrogen has been taken up. On the other hand, compound IX can be completely hydrogenated (Step K) to a compound of structure XI by continuing the hydrogenation until hydrogen uptake (2 mole-equivalents) is complete. Compounds of structure X and XI are generally known in the racemic series, and have been converted to racemic estrone and its derivatives, i.e., compounds of structure XII. Estrone methyl ether, for example, can be converted to the potent estrogen ethynylestradiol 3-methyl ether (Mestranol), an important component of antifertility preparations. A-ring aromatic steroids such as estrone methyl ether can also be converted, by reduction of the aromatic ring, to valuable 19-norsteroids.

It is known that the conversion of compound X to compound XI by catalytic hydrogenation affords a mixture of C/D-cis and C/D-trans isomers. The ratio of these isomers can be controlled depending upon the Z substituent. If Z is carbonyl, a substantial amount of C/D-cis isomer is produced, whereas if Z is $\beta$-hydroxy methylene, a preponderance of C/D-trans isomer is produced. The same considerations hold true for the 1-step hydrogenation of compound IX to compound XI. Thus, if one wishes to produce a C/D-trans steroid as final product, it is desirable before complete hydrogenation of compound IX, to have Z present as a $\beta$-hydroxy methylene group, an $\alpha$-hydrocarbyl-$\beta$-hydroxy methylene group or a suitable derivative thereof.

Compounds of formula I wherein $R_6$ is hydrogen, can also be reduced in a 1-step procedure (Step L) to compounds of formula XI by a combination hydrogenation/hydrogenolysis reaction wherein the 3a(4a),4(5) double bond is hydrogenated and the benzylic hydroxyl group in the 2'-position is hydrogenolyzed. As in Step K, this reaction is carried out by allowing the hydrogenation to proceed until it is completed, i.e. until 2-mole-equivalents of hydrogen are absorbed. The same consideration regarding the choice of Z group apply for this hydrogenation as for the hydrogenations of compounds IX and X to compound XI.

Another important aspect of the present invention is the preparation of racemic or optically active steroids having both A- and B-rings aromatic. Steroids of this nature can be prepared by a 2-step process starting with compounds of formula I. For example, compound I, wherein $R_6$ is lower acyl or lower aroyl, can be hydrogenated, as shown in Reaction Step M, to afford compounds of structure XIII. Again, as above, either a C/D-cis or C/D-trans product can be obtained depending upon the identity of the Z group.

Compounds of formula XIII can be converted, in Reaction Step N, to A,B-aromatic steroids of structure XIV by an acid-catalyzed elimination and cyclization reaction. Examples of known steroids of structure XV are equilenin, equilenin methyl ether and so forth.

In the claims, all compounds shall be construed to include, independently, the racemic form of the compound and independently, each enantiomeric form, i.e., d- and 1-configuration, unless specifically indicated otherwise.

The following examples are illustrative. All temperatures are in degrees Centigrade and all products having center of asymmetry are racemic unless specifically indicated otherwise. The "usual work-up" referred to in the following examples, consists of dilution of the reaction mixture with brine, extraction with three positions of the appropriate solvent, washing the combined extracts with brine, drying over anhydrous magnesium sulfate, filtering and concentrating under reduced pressure.

EXAMPLE 1

A solution of 33.5 g. (0.161 mole) of 3-(3-methoxybenzoyl)propionic acid in 400 ml. of 10% aqueous sodium hydroxide was stirred while a solution of 12.1 g. (0.32 mole) of sodium borohydride in 60 ml. of water was added dropwise. The resulting solution was stirred at room temperature for 4 hours then cooled in an ice-bath and cautiously treated dropwise with 240 ml. of concentrated hydrochloric acid. After stirring at 40°–50° for 45 minutes; the reaction was cooled and worked up with ether in the usual manner (the ether extracts were additionally washed with 2 portions of saturated aqueous sodium bicarbonate) giving 30 g. of viscous oily ($\pm$)-4-hydroxy-4-(3-methoxyphenyl)-butyric acid-$\gamma$-lactone. Distillation afforded 27.85 g. (90%) of colorless oil, bp. 133°–140° /0.2 mm. A sample was evaporatively redistilled giving an analytical specimen. $\nu_{max}^{CHCl_3}$ 1780 cm$^{-1}$ (lactone C=O)

Anal. Calcd. for $C_{11}H_{12}O_3$: C, 68.78; H, 6.31; Found: C, 69.00; H, 6.34

EXAMPLE 2

A solution of 19.2 g. (0.1 mole) of lactone for Example 1 in 64 ml. of dry tetrahydrofuran was coored to $-65°$ (Dry Iceisopropyl alcohol bath) and stirred under nitrogen while 80 ml. (0.16 mole) of 2M vinylmagnesium chloride in tetrahydrofuran was added dropwise over 40 minutes keeping the internal temperature at $-50°--60°$. The mixture was stirred 10 minutes more at this temperature, decomposed with 10 ml. of methanol keeping the temperature near $-50°$, and poured onto a mixture of 80 g. of ice, 6 ml. of glacial acetic acid and 16 g. of ammonium chloride The resulting mixture was extracted three times with ether and the combined extracts were treated with 50 ml. of diethylamine and dried over anhydrous magnesium sulfate for 1 hour at room temperature. After filtration, the ether solution was concentrated at reduced pressure giving 25.2 g. of yellow oil containing ($\pm$)-3-keto-6-(3-methoxyphenyl)-1-hexen-6-ol. This material was redissolved in ether and washed three times with 50 ml. portions of 1N aqueous hydrochloric acid. The combined acid extracts were washed once with ether and the combined ether solutions dried over magnesium sulfate and set aside.

The combined acid washes were chilled in an ice bath and made alkaline with 50 ml. of 10% aqueous sodium hydroxide. The mixture was worked up with ether in the usual manner giving 3.22 g. (11%) of yellow oily, ($\pm$)-1-diethylamino-3-keto-6-(3-methoxyphenyl)-hexan-6-ol equilibrium mixture, ir: $\nu_{max}^{film}$ 3330 (OH), 3180 (broad H-bonded OH), 1710 (ketone C=O, m), 1600 (anisole) cm$^{-1}$, uv: $\lambda_{max}^{EtOH}$ 215 m$\mu$ ($\epsilon$ 8780), 272 (2070), 279 (1900);

nmr: $\delta_{TMS}^{CDCl_3}$ 7.00 (complex aromatic multiplet), 5.19 (triplet, J=7 Hz, H—C—O of major component), 4.95 (multiplet H—C—O of minor component, approximately ⅓ of major component), 3.76 (—OCH$_3$ singlet), 1.05 (2 overlapping triplets of —CH$_2$CH of each component) ppm; ms: m/e 293 (M+). Tlc analysis showed a single spot.

EXAMPLE 3

A solution of 8.82 g. (0.046 mole) of lactone for Example 1 in 60 ml. of dry toluene was stirred at $-70°$ in an acetone-Dry Ice Bath while 50 ml. of a 25% solution of diisobutylaluminum hydride in toluene was added dropwise over 10 minutes. The resulting mixture was stirred at −70° for 1 hour then cautiously poured into a mixture of 70 g. of ice and 18 ml. of glacial acetic acid. The toluene layer was separated and workup with ether was carried out in the usual manner (the organic solution was additionally washed with aqueous sodium bicarbonate solution). This gave 9 g. of colorless oil which crystallized on standing. Recrystallization from benzene-hexane gave 6.87 g. (77.2%) of white solid, mp. 76°–78° . An analytical sample of (±)-5-(3-methoxyphenyl)tetrahydrofuran-2-ol was obtained by further recrystallization from benzene-hexane as white solid, mp. 76.5°–78°. ir: $\nu_{max}^{CHCl_3}$ 3450, 3625 (OH), 1600 (anisole) cm$^{-1}$ Anal. Calcd. for $C_{11}H_{14}O_3$: C, 68.01; H, 7.28; Found: C, 67.74; H, 7.16.

EXAMPLE 4

A solution of 24.9 g. (0.128 mole) of crude lactol from Example 3 in 135 ml. of dry tetrahydrofuran was added dropwise to 210 ml. of stirred, 2M vinylmagnesium chloride in tetrahydrofuran with some cooling to moderate the exothermic reaction. After the addition was complete, the solution was stirred at room temperature, under nitrogen, for 3 hours then poured into 600 ml of ice-cold aqueous ammonium chloride solution and worked up with ether in the usual manner. The residual, pale-yellow, oily (±)-6-(3-methoxyphenyl)-1-hexen-3,6-diol (28.3 g.; 99%) was sufficiently pure for further use. A sample from another identical run was chromatographed on silica gel. The materials from the fractions eluted with 3:2 benzene-ether to pure ether were combined and evaporatively distilled giving the analytical sample as a viscous, colorless oil, bp. 155°–163° (bath temp.)/0.2mm. Tlc analysis showed a single spot; ir: $\nu_{max}^{CHCl_3}$ 3400, 3600 (OH), 1600 (anisole), 990 (vinyl) cm$^{-1}$ Anal. Calcd. for $C_{13}H_{18}O_3$: C, 70.23; H, 8.18; Found: C, 70.02; H, 8.32.

EXAMPLE 5

A 2-l. 3-necked flask fitted with a mechanical stirrer was charged with 660 ml. of benzene and 284 g. of activated manganese dioxide. The dense slurry was stirred with ice-bath cooling and 42 ml. of diethylamine was added followed by 28.2 g. (0.127 mole) of crude diol from Example 4. The ice-bath was removed and the reaction mixture was stirred at room temperature for 4½ hours. The manganese dioxide was filtered with suction and the filter cake was washed thoroughly with methylene chloride. The combined filtrate and washes were concentrated at reduced pressure. The red oily residue was dissolved in ether and the ether solution was extracted 3 times with 1N aqueous hydrochloric acid and set aside. The combined acidic, aqueous solutions were basified with 10% potassium hydroxide and extracted 3 times with ether. The usual workup gave 22.4 g. (60.3%) of red oil composed of mainly the Mannich base prepared in Example 2. The material produced in this manner typically showed the following spectral properties: uv: $\lambda_{max}^{EtOH}$ 214 ($\epsilon$9990), 253 (1210), 271 (1860), 278 (1720), 303 (360) mμ ir: $\nu_{max}^{film}$ 3000–3600 (H-bonded OH), 1710 (CO), 1590, 1600 (anisole) cm$^{-1}$. Tlc analysis showed a main spot, with a minor impurity.

EXAMPLE 6

A mixture of 4 g. (0.0137 mole) of crude Mannich base mixture prepared as described in Example 5, 1.62 g. (0.0145 mole) of 2-methyl-1,3-cyclopentanedione, 15 ml. of acetic acid and 55 ml. of toluene was stirred and refluxed under nitrogen for 1 hour. After cooling, the resulting solution was diluted with ether, washed three times with water and twice with saturated aqueous sodium bicarbonate. Completion of the usual workup gave 4.097 g. of red gum. This material was recrystallized from hexane-benzene giving 2.172 g. (50.4%) of tan solid, mp 110°–112°. Another recrystallization from hexane-benzene gave 1.929 g. (44.8%) of pale yellow solid (±)-7,7a-dihydro-4-[2-(3-methoxyphenyl)-2-hydroxyethyl]-7a-methyl-1,5(6H)-indandione mp 112°–113°. This material showed a single spot on the analysis. Further recrystallization of a sample gave the analytical specimen, mp 113°–114° uv: $\lambda_{max}^{EtOH}$ 217 ($\epsilon$108000), 251 (9320), 279 (2600) mμ.

ir: $\nu_{max}^{CHCl_3}$ 3500, 3625 (OH), 1750 (cyclopentanone CO), 1660 (conjugated ketone CO), 1600 (anisole) cm$^{-1}$; mass spectrum m/e 314 (M+) nmr: $\delta_{TMS}^{CDCl_3}$ 1.17 (singlet; 3 protons 7a-CH$_3$); 3.76 (singlet, 3 protons, OCH$_3$); 4.82

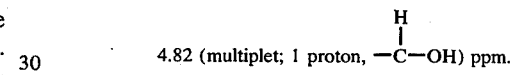
4.82 (multiplet; 1 proton, −C−OH) ppm.

ppm.

Anal. Calcd. for $C_{19}H_{22}O_4$: C, 72.58; H, 7.07; Found: C, 72.37; H, 6.81.

EXAMPLE 7

A solution of 1 g. (3.184 moles) of enedione from Example 6 and 50 mg. of p-toluenesulfonic acid in 30 ml. of toluene was stirred and refluxed for 20 minutes. The reaction mixture was cooled, diluted with ether and washed with saturated aqueous sodium bicarbonate solution. Completion of the usual work-up gave crude (±)-7,7a-dihydro-4-[m-methoxystyryl]-7a-methyl-1,5(6H)indandione as a red oil.

A sample prepared in this way (197 mg.) was chromatographed on 10 g. of silica gel. The early fractions eluted with 19:1 benzene:ether afforded 102 mg. of a yellow, oily material which was homogeneous on tlc analysis;

ir: $\nu_{max}^{film}$ 1740 (cyclopentanone C=O), 1660 (conjugated ketone C=O), 1575, 1600 (anisole), (no OH) cm$^{-1}$;

uv: $\lambda_{max}^{EtOH}$ 219 mm. ($\epsilon$18820), 271 (12250), $\lambda_{inf}^{EtOH}$ 313 (8750);

nmr: $\delta_{TMS}^{CDCl_3}$ 7.00 (center of complex multiplet, 4 aromatic protons and 2 vinyl protons), 3.80 (singlet, OCH$_3$ protons), 1.35 (singlet, 7aCH$_3$, 3 protons) ppm; Mass spectrum: m/e 296 (M+).

EXAMPLE 8

The above crude diene from Example 7 (~1 g.) in 30 ml. of toluene was stirred in an atmosphere of hydrogen in the presence of 0.2 g. of AK-4, 5% palladium on carbon (pre-equilibrated). After 30 minutes, 80 ml. of hydrogen had been absorbed (79.5 ml. theory) and the hydrogenation was stopped. The catalyst was filtered and washed with fresh toluene and the combined filtrate and washings were concentrated at reduced pressure. The residue (~1 g.) was chromatographed on 50 g. of silica gel. The fractions eluted with 19:1 and 9:1 benzene:ether afforded 0.729 g. of red oily (—)-7,7a-dihydro-4-[2-(3-methoxyphenyl)ethyl]-7a-methyl-1,5 (6H)-indandione. Evaporative distillation gave 0.675 g. (71.3%) of a viscous, yellow oil bp 180°–220° (bath)/0.01 mm. which was homogeneous on tlc analysis; ir: $\nu_{max}{}^{film}$ 1740 (cyclopentanone C=O), 1660 (conjugated ketone), 1600 (anisole), 780, 690 cm$^{-1}$; uv: $\lambda_{max}{}^{EtOH}$ 220 m$\mu$ ($\epsilon$10400), 251 (8300). This material has previously been converted to racemic estrone.

EXAMPLE 9

A mixture of 2.76 g. (8.8 mmoles) of pure ketol from Example 6 and 28 ml. of ethanol was stirred rapidly and cooled in a −10° ice-salt bath while 9.2 ml. (2.67 mmoles) of 0.291M ethanolic sodium borohydride was added dropwise over a 10 minute period. The reaction mixture was stirred at −5° to −5° for 50 minutes, then decomposed with 3N aqueous hydrochloric acid. Workup with ether in the usual manner gave 2.917 g. of (±)-1$\beta$-hydroxy-7,7a-dihydro-4[2-(3-methoxyphenyl)-2-hydroxyethyl]-7a$\beta$-methyl-5(6H)indanone as a tan foam which could not be induced to crystallize Tlc analysis indicated a single spot, and no trace of the starting material; $\nu_{max}{}^{film}$ 3450 (OH), 1640 (conjugated ketone CO) cm$^{-1}$. This material was used without further purification.

The crude diol (2.9 g.) was hydrogenated in 80 ml. of ethanol in the presence of 250 mg. of AK-4 5% palladium on carbon. After 20 hours, 361 ml of hydrogen had been absorbed. The catalyst was filtered and the filtrate concentrated at reduced pressure. The residue was hydrogenated in 75 ml. of ethanol with 250 mg. of fresh AK-4 catalyst for 20 hours at the end of which time 91 ml. of hydrogen had been absorbed (452 ml. total; theory for 2 moles-440 ml.). The catalyst was filtered and the filtrate concentrated at reduced pressure giving 2.763 g. of pale yellow glass containing (±)-1$\beta$-hydroxy-3a,4,7,7a-tetrahydro-4-[2-(3-methoxyphenyl)ethyl]-7a$\beta$-methyl-5(6H)indanone.

This material was dissolved in 50 ml. of acetone and stirred with ice-bath cooling while 5 ml. of 8N Jones reagent was added dropwise over 20 minutes. The red mixture was stirred for 5 minutes in the ice-bath then decomposed with 2-propanol. The usual workup with ether afforded 2.75 g. of yellow oil composed mainly of (±)-3a,4,7,7a-tetrahydro-4]2-(3-methoxyphenyl)-ethyl]-7a$\beta$-methyl-1,5(6H)indandione; ir: $\nu_{max}{}^{CHCl_3}$ 1750 (cyclopentanone CO), 1710 (cyclohexanone CO) cm$^{-1}$.

The above, crude diketone mixture (2.75 g.) in 60 ml. of methanol was stirred while 12 ml. of 10N aqueous hydrochloric acid was added. The resulting mixture was stirred at room temperature for 4 hours then cooled in ice and the precipitated solid filtered with suction and washed with a little ice-cold methanol. After drying under high vacuum, 0.667 g. (27% based on ketol) of white solid, mp 130°–137° which was homogeneous on tlc analysis was obtained. This material was an approximately 2:1 mixture of two isomers as evidenced by the following properties: $\lambda_{max}{}^{EtOH}$ 263 ($\epsilon$ 17300) m$\mu$; ir: $\nu_{max}{}^{CHCl_3}$ 1740 (cyclopentanone CO), 1600 (anisole) cm$^{-1}$;

$\delta_{TMS}{}^{CDCl_3}$ 0.91 (singlet, $C_{13}$—CH$_3$), 1.12 (singlet, $C_{13}$—CH$_3$) (these peaks in a ratio of 2:1 respectively), 3.81 (singlet, OCH$_3$), 6.15 (multiplet, $C_{11}$-H) ppm; mass spectral molecular ion m/e 282. Gc analysis on a 1% DEGA/Anak ABS column, at 200°, with a nitrogen carrier gas flow rate of 100 mls/min showed 2 peaks: retention time 10.5 minutes (31.2%) and 14.5 minutes (68.8%).

A sample of this material was separated by preparative gas chromatography (Autoprep 70S; 20% SE-30 on Anak A (⅜ inch × 10 ft.) aluminum column; 220°; 150 ml/min nitrogen carrier gas flow rate; 5 mg. injections of 10% solution in xylene-chloroform). The main component (98% pure) was a colorless solid, racemic 9(11) dehydroestrone methyl ether m.p. 146°–148°.

uv: $\lambda_{max}{}^{EtOH}$ 263 m$\mu$ (18750), 293 (3220), $\lambda_{infl.}{}^{EtOH}$ 310 (2100); nmr:

$\delta_{TMS}{}^{CDCl_3}$ 7.53 (doublet, J=8Hz, C$_1$ proton), 6.73 (multiplet, C$_2$ and C$_4$ protons), 6.23 (multiplet, C$_{11}$ proton), 3.76 (singlet, OCH$_3$), 0.91 (singlet, C$_{13}$CH$_3$) ppm; mass spectrum: m/e 282 (M+). Reported for racemic 9(11)dehydroestrone methyl ether m.p. 146°–147°; $\lambda$max 264 m$\mu$ ($\epsilon$ 18800). A small sample of the minor component racemic 14$\beta$-8(9)-dehydroestrone methyl ether was isolated (98% purity) as a solid, m.p. 75°–85°. uv: $\lambda_{max}{}^{EtOH}$ 272 m$\mu$ ($\epsilon$16800); nmr: $\delta_{TMS}{}^{CDCl_3}$ 7.02 (doublet, J=9Hz, C$_1$ proton), 6.62 (multiplet, C$_2$ and C$_4$ protons), 3.76 (singlet, OCH$_3$, 3 protons), 2.69 (multiplet, 2 C$_{11}$ protons) 1.06 (C$_{13}$CH$_3$ singlet, 3 protons) ppm. Reported for (+)−14$\beta$-8(9)-dehydroestrone methyl ether: uv: $\lambda_{max}{}^{EtOH}$ 273 m$\mu$ ($\epsilon$16600); nmr: $\delta_{TMS}{}^{CDCl_3}$ 3.79 (—OCH$_3$), 2.73 (C$_{11}$ protons), 1.08 (C$_{13}$—CH$_3$) ppm.

EXAMPLE 10

A 0.5 g. (1.59 mmoles) sample of pure ketol from Example 6 was allowed to stand at room temperature in a solution of 5 ml. of pyridine and 2.5 ml. of acetic anhydride for 27 hours. The solvents were partially removed at reduced pressure and the residue was poured into saturated aqueous sodium bicarbonate and worked up with ether (the ether extracts were additionally washed twice with 1N hydrochloric acid) giving 0.573 g. of the oily acetate. This material showed a single spot on tlc analysis. After drying thoroughly, it showed the following spectral properties: uv: $\lambda_{max}{}^{EtOH}$ 220 ($\mu$11010), 249 (9190), 275 (3040), 281 (2620) m$\mu$; ir: $\nu_{max}{}^{CHCl_3}$ 1750 (cyclopentanone, acetate C=O), 1670 (conjugated ketone CO), 1600 (anisole) cm$^{-1}$; mass spectral molecular weight m/e 356; nmr: $\delta_{TMS}{}^{CDCl}$ 1.15 (singlet, 7a-CH$_3$),

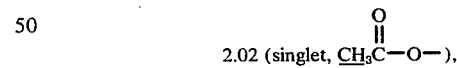
2.02 (singlet, C$\underline{H}_3$C—O—), 3.78 (singlet, -OC$\underline{H}_3$),

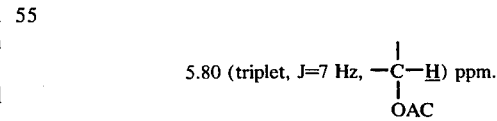
5.80 (triplet, J=7 Hz, —C—$\underline{H}$) ppm.
OAC

A 0.526 g. (1.48 mmoles) sample of the crude acetate was dissolved in 4.6 ml. of ethanol and the solution was stirred at −10° (ice-salt bath) while 1.56 ml. of a 0.291 M ethanolic sodium borohydride solution was added dropwise from a syringe. The resulting mixture was stirred in the cold bath for 40 minutes then decomposed with 1N aqueous hydrochloric acid. Work-up with ether in the usual manner gave 0.545 g. of a yellow gum which was homogeneous on tlc analysis. This material, (±)-1β-hydroxy-7,7a-dihydro-4[2-(3-methoxyphenyl)-2-acetoxyethyl]-7a -methyl-5(6H)-indanone, was used without further purification and showed the following spectral properties: ir: $\nu_{max}^{film}$ 3400 (OH), 1730 (ester C=O), 1650 (conjugated ketone C=O), 1600 (anisole), 1230 (acetate) cm$^{-1}$; uv: $\lambda_{max}^{EtOH}$ 219 mμ (ε9210), 248 (9300); nmr: $\delta_{TMS}^{CDCl_3}$ 7.10 (multiplet, 4 aromatic protons), 5.84 (triplet, J=8 Hz, H-C—O, 1 proton), 3,82 (singlet, 3—OCH$_3$ protons), 2.04 (singlet, CH$_3$C=O), 1.02 (singlet, 3 C$_{7a}$—CH$_3$ protons) ppm; mass spectrum: m/e 358 (M+).

EXAMPLE 11

A 0.742 g. (2.08 mmoles) sample of acetoxy ketol from Example 10 was hydrogenated in 30 ml. of ethanol, over 0.2 g. of pre-equilibrated palladium on barium sulfate at one atmosphere and room temperature. After 5.67 hours, 53 ml. of hydrogen had been consumed (theory for 1 mole equivalent-52 ml.). The catalyst was filtered with suction and washed with fresh ethanol. The combined filtrate and washes were concentrated at reduced pressure giving 0.736 g. of a cloudy glass.

This material was chromatographed on 37.5 g. of silica gel. Elution with 1:1 benzene:ether gave 109 mg. of an oil which was a mixture of isomers of (±)-1β-hydroxy-3a, 4,7,7a-tetrahydro-4[2-(3-methoxyphenyl)-2-acetoxyethyl]-7aβ-methyl-5(6H)-indanone; ir: $\nu_{max}^{film}$ 3450 (OH), 1730 (ester C=O), 1700 (cyclohexanone C=O), 1590 (anisole) cm$^{-1}$ (no conjugated ketone present).

A sample of hydrogenation product prepared in this way (0.191 g.; 0.53 mmole) was dissolved in 5 ml. of acetone. The resulting solution was stirred and cooled to 0°-5° (ice-bath) while 0.19 ml. of Jones reagent was added from a syringe. The resulting red mixture was stirred for several minutes then decomposed with 2-propanol. Work-up with ether in the usual manner gave 0.171 g. of (±)-3a,4,7,7a-tetrahydro-4[2-(3-methoxyphenyl)-2-acetoxyethyl]-7aβ-methyl-1,5(6H)-indandione which was homogeneous on tlc analysis; ir: $\nu_{max}^{film}$ 1735 (ester and cyclopentanone C=O), 1700 (cyclohexanone C=O), 1590 (anisole) cm$^{-1}$. Material from a similar run showed the following spectral properties: uv: $\lambda_{max}^{EtOH}$ 215 mλ (μ 6960), 272 (2030), 279 (1840); nmr: $\delta_{TMS}^{CDCl_3}$ 6.85 (aromatic multiplet), 5.90 (triplet, J=8 Hz, H—C—O), 3.87 (singlet, OCH$_3$), 2.02 (singlet, CH$_3$C=O), 1.26 (singlet, C$_{7a}$—CH$_3$), 1.02 (singlet, C$_{7a}$—CH$_3$ approximately 2.33 times the intensity of the 1.26 signal) ppm; mass spectrum: m/e 358 (M+).

An ice cold solution of the above diketo acetate (0.171 g.; 0.475 mmole) in 3 ml. of methanol was stirred while 0.625 ml. of 10 N aqueous hydrochloric acid was added. The resulting solution was stirred at 0°-5° for 10 minutes then at room temperature for 3.5 hours. Workup with ether in the usual manner gave 0.162 g. of oily product.

This material was stirred and refluxed in 5 ml. of benzene containing 25 mg. of p-toluenesulfonic acid monohydrate. After cooling the solution was diluted with ether, washed once with aqueous sodium bicarbonate solution, dried (anhydrous magnesium sulfate) filtered and concentrated at reduced pressure giving 0.138 g. of semi-crystalline residue. Chromatography on 7.5 g. of silica gel gave 63 mg. of pure, racemic equilenin methyl ether (eluted with 49:1 benzene:ether; tlc:one spot). Recrystallization from ethanol gave colorless plates, m.p. 183°-186° (reported m.p. 185°-186°). The ir, uv and nmr spectra and tlc chromatographic behavior of the racemic material were identical to those of d-equilenin methyl ether prepared by methylation of (+)-equilenin as described by A. Wilds et al.

EXAMPLE 12

A slurry of 14.9 g. (0.0788 mole) of 3-(3-methoxybenzoyl)-propionitrile in 120 ml. of absolute ethanol was stirred in an ice-salt bath at −5° to 0° C. while a solution of 1.5 g. (0.0396 mole) of sodium borohydride in 100 ml. of absolute ethanol was added dropwise over a 30 minute period. The reaction mixture was gradually allowed to warm to room temperature as it was stirred for 1¼ hour. The mixture was then poured into a separatory funnel containing 250 ml. of ether and 250 ml. of water. The aqueous layer was separated, cooled, brought to a pH of 5–6 by slowly adding 1N aqueous hydrochloric acid and extracted three times with ether. The ether layers were combined, washed with brine, dried and filtered. Solvent removal gave 14.2 g. (94.3%) of crude racemic 4-hydroxy-4-(3-methoxyphenyl)butyronitrile as a colorless liquid which was sufficiently pure for further use.

A sample from a similar run was chromatographed on silica gel (50 parts; eluted with 9:1 benzene:ether) and evaporatively distilled to give an analytical sample as a pale yellow liquid; bp 130°-175° (bath temp.)/0.07 mm. This material showed a single spot on TLC analysis; uv: $\lambda_{max}^{EtOH}$ 219 (ε6570), 273 (1910), 281 (1730) mμ;

ir: $\nu_{max}^{CHCl_3}$ 3475, 3600 (OH), 2250 (C≡N), 1590, 1600 (anisole) cm$^{-1}$; MS: m/e 191 (M+)

Anal. Calcd. for C$_{11}$H$_{13}$NO$_2$: C, 69.09; H, 6.85; N, 7.33. Found: C, 68.83; H, 6.80; N, 7.16.

EXAMPLE 13

A solution of 56.1 g. (0.294 mole) of crude hydroxynitrile prepared as in Example 12, 44.4g. (0.3 mole) of phthalic anhydride and 160 ml. of anhydrous pyridine (dried over alumina I) was heated at 100° C. for 5 hours. The reaction mixture was cooled, poured into a mixture of 300 g. of ice and 1 liter of 3N aqueous hydrochloric acid and the resulting acidic aqueous solution was extracted three times with ether. The ether extracts were combined and extracted with 10% aqueous sodium carbonate solution then discarded. The alkaline extracts were combined, washed with ether then carefully acidified to pH 1 with 10% aqueous hydrochloric acid saturated with sodium chloride and extracted three times with chloroform. The chloroform extracts were combined, washed with brine, dried and filtered. Solvent removal gave 93.6 g. (93.8%) of crude racemic-[3-cyano-1-(3-methoxyphenyl)]-1-propyl hemiphthalate as a brown oil which was used without purification.

A crude sample from a similar experiment showed the following spectral data: uv: $\lambda_{max}^{EtOH}$ 273 (ε3170), 279 (ε3040), $\lambda_{infl}^{EtOH}$ 222 (ε15060) mμ;

ir: $\nu_{max}^{CHCl_3}$ 3400-3050 (broad H-bonded OH), 2250 (C≡N), 1740 (ester C=O), 1710 (acid C=O), 1605, 1595 (anisole) cm$^{-1}$; mass spectrum m/e 339 (M+).

EXAMPLE 14

To a solution of 93.6 g. (0.276 mole) of crude hemiphthalate from Example 13 in 200 ml. of acetonitrile was added 35 g. (0.2885 mole) of d-(+)-α-methylbenzylamine in 20 ml. of acetonitrile. The mixture was heated on the steam bath for 5 minutes, allowed to cool gradually, and then allowed to stand over the weekend at room temperature. The white solid obtained was recrystallized twice from acetonitrile giving 25.3 g. (39.8%) of pure R-(−)-[3-cyano-1-(3-methoxyphenyl)]-1-propyl hemiphthalate d-(+)-α-methylbenzylamine salt as a white solid, m.p. 124.5°–126°, $[\alpha]_D^{25}$ −51.08° (in ethanol, C = 1%).

The analytical specimen showed m.p. 122°–123.5°; $[\alpha]_D^{25}$ −51.57° (ethanol, 1%); NMR: $\delta_{TMS}^{CDCl_3}$ 8.37 (multiplet, 3 protons, N$\underline{H}_3^+$), 7.23 (multiplet, 13 protons, aromatic), 5.85 (multiplet, 1 proton, H—C—O—), 4.16 (multiplet, 1 proton H$_3$C—C—$\underline{H}$), 3.72 (singlet, 3 protons, —OC$\underline{H}_3$), 2.19 (multiplet, 4 protons, —C$\underline{H}_2$C$\underline{H}_2$CN), 1.38 doublet, J=7, Hz, 3 protons, —C$\underline{H}_3$) ppm.

Anal. Calcd. for $C_{27}H_{28}N_2O_5$: C, 70.42; H, 6.13; N, 6.08. Found: C, 70.22; H, 5.96; N, 5.86.

EXAMPLE 15

The mother liquor from the crystallization of the salt in Ex. 14 was concentrated at reduced pressure to give 189 g. of a brown oil which contained some acetonitrile. This material was treated with ether and an excess of 3N HCl. The organic layer was separated and the aqueous phase was extracted 3 times with ether. The ether layers were combined, washed with brine, dried and filtered. Solvent removal gave 114 g. (0.337 mole) of crude hemiphthalate as a brown oil. This material was taken up in 200 ml. of acetonitrile and treated with 41 g. (0.338 mole) of 1-(−)-α-methylbenzylamine in 50 ml. of acetonitrile. The mixture was heated on the steam bath for 15 minutes, allowed to cool slightly, and then allowed to stand over the weekend at room temperature. The white solid obtained was recrystallized twice from acetonitrile giving 36.3 g. of pure S-(+)-[3-cyano-1-(3-methoxyphenyl)]-1-propyl hemiphthalate 1-(−)-α-methylbenzylamine salt as a white solid, m.p. 132°–133°, $[\alpha]_D^{25}$ +55.75° (ethanol, C = 1%), NMR: $\delta_{TMS}^{CDCl_3}$ 8.45 (multiplet, 3 protons, N$\underline{H}_3^+$), 7.24 (multiplet, 13 protons, aromatic), 5.88 (multiplet, 1 proton, -C$\underline{H}$-O), 4.18 (multiplet, 1 proton, H$_3$C—C—$\underline{H}$), 3.75 (singlet, 3 protons, —OC$\underline{H}_3$), 2.20 (multiplet, 4 protons, —CH$_2$CH$_2$CN), 1.37 (doublet, J=7 Hz, 3 protons, —C$\underline{H}_3$) ppm.

Anal. Calcd. for $C_{27}H_{28}N_2O_5$: C, 70.42; H, 6.13; N, 6.08. Found: C, 70.64; H, 6.27; N, 6.08.

EXAMPLE 16

To a separatory funnel containing 150 ml. of ether and 75 ml. of 3N aqueous hydrochloric acid was added 10 g. (0.0217 mole) of the S-salt from Example 15. After shaking until the salt was dissolved the ether layer was separated and washed with 25 ml. of 3N aqueous hydrochloric acid. The acidic aqueous solutions were combined and extracted three times with ether. The ether layers were combined, washed with brine, dried and filtered. Solvent removal gave the free hemiphthalate $[\alpha]_D^{25}$ +21.77° (ethanol, c 1%) as a colorless oil. This material was treated with 160 ml. of 10% aqueous sodium hydroxide and heated at reflux with stirring for 5 hours. The reaction mixture was cooled, washed once with ether (discard), acidified to pH 1 with 3N aqueous hydrochloric acid and stirred for 1¾ hour at room temperature. The reaction mixture was saturated with sodium chloride and extracted three times with ether. The ether extracts were combined, washed with saturated aqueous sodium bicarbonate solution and brine, then dried and filtered. Solvent removal gave a colorless oil which was evaporatively distilled to give 3.5 g. (83.8%) of S-(−)-4-hydroxy-4-(3-methoxyphenyl)-butyric acid γ-lactone as a colorless liquid, b.p. 170°–185° (bath temp.)/0.1 mm., $[\alpha]_D^{25}$ −12.05° (ethanol, c = 1%). TLC analysis showed a single spot JR:$\nu_{max}^{CHCl_3}$ 1780 (γ-lactone C=O), 1605, 1590 (anisole) cm$^{-1}$; mass spectrum m/e 192 (M$^+$); NMR: $\delta_{TMS}^{CDCl}$ 7.29 multiplet, 1 proton, aromatic), 6.87 (multiplet, 3 protons, aromatic), 5.47 (triplet, J=7 Hz, 1 proton, -O-C-$\underline{H}$), 3.79 (singlet, 3 protons, OC$\underline{H}_3$), 2.60 (multiplet, 4 protons, -CH$_2$CH$_2$—) ppm.

Anal. Calcd. for $C_{11}H_{12}O_3$: C, 68.73; H, 6.29. Found: C, 68.45; H, 6.34.

EXAMPLE 17

To a separatory funnel containing 400 ml. of ether and 300 ml. of 3N aqueous hydrochloric acid was added 36.7 g. (0.0798 mole) of the R-salt from Example 14. After shaking until the salt was dissolved the ether layer was separated and washed with 100 ml. of 3N aqueous hydrochloric acid. The acidic aqueous solutions were combined and extracted three times with ether. The ether layers were combined, washed with brine, dried and filtered. Solvent removal gave the hemiphthalate as a colorless oil. A sample from a similar experiment showed $[\alpha]_D^{25}$ −22.02° (ethanol, c 1%).

This material was treated with 600 ml. of 10% aqueous sodium hydroxide and heated at reflux, with stirring for 5 hours. The reaction mixture was cooled, washed once with ether, acidified to pH 1 with 3N aqueous hydrochloric acid (~600 ml.) and stirred for 1¾ hour at room temperature. The reaction mixture was then saturated with sodium chloride and extracted three times with ether. The ether extracts were combined, washed with saturated aqueous sodium bicarbonate solution and brine, then dried and filtered. Solvent removal gave 11.9 g. of crude lactone as a colorless oil. The aqueous sodium bicarbonate wash was cautiously acidified with concentrated hydrochloric acid to pH 1 and after working up the acidic aqueous solution with ether in the above manner 1.7 g. of additional crude lactone was obtained as a colorless oil to give a total of 13.6 g. (88.8%) of R-(+)-4-hydroxy-4-(3-methoxyphenyl)butyric acid γ-lactone.

A sample was evaporatively distilled to give a colorless liquid, b.p. 165°–170° (bath temp.)/0.2 mm. TLC analysis showed a single spot; IR: $\nu_{max}^{CHCl_3}$ 1780 (γ-lactone C=O), 1605, 1595 (anisole) cm$^{-1}$; mass spectrum m/e 192 (M$^+$); NMR: $\delta_{TMS}^{CDCl_3}$ 7.27 (multiplet, 1 aromatic proton), 6.86 (multiplet, 3 aromatic protons), 5.44 (triplet, J=7 Hz, 1 proton, $\underline{H}$—C—O), 3.78 (singlet, 3 protons, OC$\underline{H}_3$), 2.60 (multiplet, 4 protons, —C$\underline{H}_2$C$\underline{H}_2$—) ppm.

The analytical specimen, b.p. 170°–180° (bath temp.)/0.1 mm. showed $[\alpha]_D^{25}$ +12.93° (ethanol, C=1%).

Anal. Calcd. for $C_{11}H_{12}O_3$: C, 68.73; H, 6.29; Found: C, 68.44; H, 6.18.

EXAMPLE 18

A solution of 1.873 g. (0.0098 mole) of lactone from Example 17 in 20 ml. of dry toluene was stirred at ~70° in an acetone-dry ice bath while 11 ml. of a 25% solution of diisobutylaluminum hydride in toluene was added dropwise over a three minute period. The reaction mixture was stirred at ~−70° for 1 hour and then cautiously poured into a mixture of 15 g. of ice and 4 ml. of glacial acetic acid. The resulting mixture was diluted with brine and the organic layer was separated. The acidic aqueous solution was extracted three times with ether. The organic solutions were combined, washed with aqueous saturated sodium bicarbonate solution and brine, then dried and filtered. Solvent removal gave 1.888 g. of crude 5R-(3-methoxyphenyl)-tetrahydrofuran-2-ol as a colorless oil. TLC analysis showed the absence of starting material; IR: $\nu_{max}^{film}$ 3400 (OH), 1600, 1590 (anisole) cm$^{-1}$.

EXAMPLE 19

A solution of 1.635 g. (0.0084 mole) of the crude lactol from Example 18 in 20 ml. of dry tetrahydrofuran was added dropwise to 15.0 ml. of stirred 2M vinylmagnesium chloride in tetrahydrofuran over a 10 minute period with ice-bath cooling. The reaction mixture was allowed to stir for 3 hours at room temperature then poured into 40 ml. of ice-cold aqueous ammonium chloride solution and extracted three times with ether. The ether extracts were combined, washed with brine, dried and filtered. Solvent removal gave 1.98 g. of the crude 6R-(3-methoxyphenyl)-1-hexen-3,6-diol as a pale yellow oil.

EXAMPLE 20

Into a 250 ml. three-necked flask fitted with a mechanical stirred was placed 40 ml. of dry benzene and 18 g. of activated manganese dioxide. The slurry was cooled in an ice-bath and 3 ml. of diethylamine was added followed by 1.98 g. (assume 0.0084 mole) of crude vinyl diole from Example 19 in 20 ml. of dry benzene. The ice bath was removed and the reaction mixture was stirred at room temperature for 4½ hr. The manganese dioxide was filtered and washed thoroughly with methylene chloride. The combined filtrate and washings were concentrated at reduced pressure giving a red oil which was dissolved in ether and extracted three times with 1N agueous hydrochloric acid.

The acidic aqueous solutions were combined, made alkaline with 10% aqueous potassium hydroxide solution and extracted three times with ether. The ether extracts were combined, washed with brine, dried and filtered. Solvent removal gave 1.695 g. of a red oil composed mainly of 6R-1-diethylamino-3-keto-6-(3-methoxyphenyl)-hexan-6-ol equilibrium mixture. Material prepared in this way typically showed the following IR: $\nu_{max}^{film}$ 3600–3000 (H-bonded OH), 1715 (ketone C=O of open form), 1685 (shoulder, trace acetophenone type impurity), 1605, 1590 (anisole) cm$^{-1}$. TLC analysis (9:1 benzene-triethylamine) showed essentially a single spot.

EXAMPLE 21

A mixture of 8.3 g. (0.0283 mole) of the crude Mannich base from Example 20, 3.36 g. (0.0300mole) of 2-methyl-1,3-cyclopentanedione, 30 ml. of glacial acetic acid and 100 ml. of toluene was stirred and heated at reflux for 1 hr. The reaction mixture was cooled, diluted with ether, washed three times with water, twice with saturated aqueous sodium bicarbonate solution, once with brine, then dried and filtered. Solvent removal gave 8.2 g. of crude, red, oily product. This material was chromatographed on 400 g. of silica gel. The fractions eluted with 1:1 benzene:ether and ether afforded 5.5 g. (62%) of the mixture of 7,7a-dihydro-4-[2R-(3-methoxyphenyl)-2R-hydroxyethyl]-7aS-methyl-1,5(6H)-indandione and 7,7a-dihydro-4-[2R-(3-methoxyphenyl)-2R-hydroxyethyl]-7aR-methyl-1,5(6H)-indandione with the former predominating as an orange oil $[\alpha]_D^{25}$ +117.59° (ethanol, C=1%). This material was essentially homogeneous on TLC analysis; UV: $\lambda_{max}^{EtOH}$ 219 ($\epsilon$10410), 252 ($\epsilon$8675), 279 ($\epsilon$2820)m$\mu$; IR: $\nu_{max}^{CHCl_3}$ 3450, 3600 (OH), 1750 (cyclopentanone C=O), 1655 (conjugated ketone C=O), 1590, 1600 (anisole) cm$^{-1}$; mass spectrum m/e 314 (M$^+$); NMR: $\delta_{TMS}^{CDCl_3}$ 4.82 (multiplet, 1proton, H—C—OH), 3.72 (singlet, 3protons, —OCH$_3$), 1.13 (singlet, 1 proton, C$_{7a}$—CH$_3$)ppm.

EXAMPLE 22

A solution of 0.493 g. (1.57 mmoles) of the hydroxy enedione mixture from Example 21 and 50 mg. of p-toluenesulfonic acid monohydrate in 15 ml. of toluene was stirred and heated at reflux for 20 minutes. The reaction mixture was cooled, diluted with ether, washed with saturated aqueous sodium bicarbonate solution and brine, then dried and filtered. Solvent removal gave the crude diene as a red oil which was hydrogenated in 30 ml. of toluene in the presence of 0.15 g. of AK-4, 5% palladium on carbon (preequilibrated). After 15 minutes, 39.2 ml. of hydrogen had been absorbed (39.3 ml). theory) and the hydrogenation was stopped. The catalyst was filtered, washed with ether and the combined filtrate and washings were concentrated at reduced pressure to give 0.46 g. of the crude enedione as a red oil. This material was chromatographed on silica gel (50 g.) to give 0.352 g. of an orange oil (eluted with 9:1 benzene: ether). Evaporative distillation gave 0.335 g. (71.6 %) of a mixture of the S-isomer and racemic 7,7a-dihydro-4[2-(3-methoxyphenyl)ethyl]-7a-methyl-1,5(6H)-indandione as a yellow oil, b.p. 145°–175° (bath)/0.01 mm which was homogeneous on TLC analysis; $[\alpha]_D^{25}$ +149.68° (benzene, C ½%); $\lambda_{max}^{EtOH}$ 249 ($\epsilon$8940).

Preparative gas chromatographic purification of a sample prepared in this way was carried out using an F and M model 320 instrument on an 8 ft. × ½ in. 10% SE30 on 70–80 m Chrom. W AW-DMCS column at 280° and the helium carrier gas flow rate at ~2-2.5 ml/sec. The major peak (~94%; retention time 8.8 min.) was collected and evaporative distillation of this material gave a mixture of the S-isomer and racemic enedione as a pale yellow oil, b.p. 150–180/0.03 mm; $[\alpha]_D^{25}$ +153.60° (benzene, 0.5%); IR: $\nu_{max}^{film}$ 1750 (cyclopentanone C=O), 1665 (conjugated ketone), 1600, 1590 (anisole) cm$^{-1}$; UV: $\lambda_{max}^{EtOH}$ 219 ($\epsilon$11,115), 250 ($\epsilon$8770), 279 ($\epsilon$2470). The spectra were essentially identical to those of the pure racemic enedione and the pure S-enedione prepared in other experiments.

ORD (c 0.3178%, dioxane, 23°): $[\phi]_{700}$ +254.8°, $[\phi]_{589}$+396.4°, $[\phi]_{370}$+5346.3°, $[\phi]_{366}$+5281.1°, $[\phi]_{355}$ 6519.8°, $[\phi]_{349}$ +4824.7°, $[\phi]_{342}$ +5607.4°. $[\phi]_{335}$ +4694.3°. $[\phi]_{324}$ +8662.1°, $[\phi]_{313}$ +2980.5°, $[\phi]_{309}$ 0°, $[\phi]_{271}$ −30736.3, $[\phi]_{258}$ −4303.8, $[\phi]_{244}$ 0°, $[\phi]_{230}$ +45173°, $[\phi]_{208}$ (last) +2528.5°.

Anal. Calcd. for $C_{19}H_{22}O_3$: C, 76.48; H, 7.42.
Found: C, 76.21;H, 7.56.

EXAMPLE 23

A mixture of 2.6 g. (8.3 mmoles) of the hydroxy enedione mixture from Example 21, 3.65 g. (16.6 mmoles) of 4-bromobenzoyl chloride and 75 ml. of pyridine (dried over alumina I) was stirred at room temperature overnight. The reaction mixture was then treated with 25 ml. of water and allowed to stir for 15 minutes at room temperature before acidification with 3N aqueous hydrochloric acid and then extracted three times with ether-methylene chloride. The organic extracts (which contained some insoluble material) were combined, washed once with water, twice with aqueous saturated sodium bicarbonate solution, once with brine, then dried and filtered. Solvent removal gave a yellow solid residue which was chromatographed on 250 g. of silica gel. The fractions eluted with 9:1 and 4:1 benzene:ether afforded 3.388 g. (82.3%) of yellow solid (mixture of p-bromobenzoates).

This material was recrystallized four times from ethanol giving 1.9 g. (46.3%) of pure (+)-7,7a-dihydro-4-[2R-(3-methoxyphenyl)-2R-(4-bromobenzoyloxy)-ethyl]-7aS-methyl-1,5-(6H)-indandione as white crystals, m.p. 126°–125° (homogenous on TLC analysis); $[\alpha]_D^{25}$ +143.85° (benzene, C=0.5); UV: $\lambda_{max}^{EtOH}$ 247 m$\mu$ ($\epsilon$29450); IR: $\nu_{max}^{CHCl_3}$ 1745 (cyclopentanone C=O), 1725 (ester C=O), 1670 conjugated ketone C=O), 1590 (anisole) cm$^{-1}$; mass spectrum m/e 496 (M+);

NMR: $\delta_{TMS}^{CDCl_3}$ 7.71 (A$_2$B$_2$ multiplet, 4 protons, p-BrC$_6$H$_4$—C—), 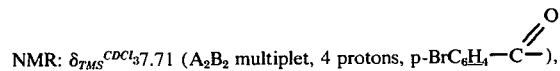

7.05 (multiplet, 4 protons, m-CH$_3$OC$_6$H$_4$-), 6.08 (Triplet, J 7 Hz, 1 proton, H-C-O), 3.78 (singlet, 3 protons, -OCH$_3$), protons, C$_{7a}$-CH$_3$) ppm.

Anal. Calcd. for C$_{26}$H$_{25}$BrO$_5$: C, 62.78; H, 5.07; Br, 16.06.
Found: C, 63,08; H, 5.01; Br, 15.97.

The mother liquors from the first recrystallization above were concentrated. The NMR spectrum of the semi-crystalline residue showed two C$_{7a}$—CH$_3$ resonance singlets at $\delta$1.11 and $\delta$1.08 in an approximately 1:1 ratio. The TLC of this material showed no impurities present.

EXAMPLE 24

A solution of 1.84 g. (3.71 mmoles) of the pure bromobenzoate from Example 23 and 0.3 g. of p-toluenesulfonic acid monohydrate in 50 ml. of toluene was stirred at reflux for 1½ hr. The reaction mixture was cooled, diluted with ether, washed with aqueous saturated sodium bicarbonate solution and brine, then dried and filtered. Solvent removal gave an orange-yellow solid which was chromatographed on silica gel (60 g.) to give 0.9 g. of an orange-yellow solid (eluted with 4:1 and 9:1 benzene:ether). Recrystallization from ethanol afforded 0.732 g. (66.5%) of the S-(+)-7,7a-dihydro-4(m-methoxystyryl)-7a-methyl-1,5(6H)-indanedione as yellow needles, m.p. 111.5°–112.5°; homogeneous on TLC analysis.

An analytical specimen was obtained as yellow needles, m.p. 112°–112.5° by further recrystallization of a sample from ethanol; $[\alpha]_D^{25}$ +164.35° (benzene, C=0.5); UV: $\lambda_{max}^{EtOH}$ 219 ($\epsilon$23520), 279(16200), $\lambda_{sh}^{EtOH}$ 315($\epsilon$12800)m$\mu$; $\nu_{max}^{CHCl_3}$ 1750 (cyclopentanone C=O), 1670 (conjugated ketone), 1640 (-C=C- weak), 1600, 1585 (anisole) cm$^{-1}$; NMR: $\delta_{TMS}^{CDCl_3}$ 6.95 (multiplet, 4 aromatic and 2 vinyl protons), 3.78 (singlet, 3 protons, -OCH$_3$), 1.34 (singlet, 3 protons, C$_{7a}$—CH$_3$) ppm.

Anal. Calcd. for C$_{19}$H$_{20}$O$_3$: C, 77.00 H, 6.80.
Found: C, 77.07; H, 6.98.

EXAMPLE 25

The pure diene from Example 24 (0.407 g; 1.38 mmoles) was hydrogenated in 25 ml. of dry toluene in the presence of 0.2 g. of AK-4, 5% palladium on carbon (pre-equilibrated). After 25 minutes, 37.5 ml. of hydrogen had been absorbed (34.4 ml. theory) and the hydrogenation was stopped. The catalyst was filtered, washed with ether and the combined filtrate and washings were concentrated at reduced pressure. The residual, colorless oil was chromatographed on silica gel (20 g.) to give 0.401 g. (97.8 %) of S-(+)-7,7a-dihydro-4-[2-(3-methoxyphenyl)ethyl]-7a-methyl-1,5(6H)-indandione as a colorless oil (eluted with 9:1 and 4:1 benzene:ether). A sample from a similar run was rechromatographed on silica gel and evaporatively distilled to give an analytical specimen as a pale yellow oil, b.p. 170°–185° (bath temp.)/0.05 mm which was homogeneous on TLC analysis; $[\alpha]_D^{25}$ +195.05° (benzene, C=0.5); UV: $\lambda_{max}^{EtOH}$ 220 ($\epsilon$11470), 250 ($\epsilon$9380), 278 ($\epsilon$2630); ORD: (C 0.5975%, dioxane, 23°) $[\phi]_{700}$ +349.1°, $[\phi]_{589}$ +528.1°, $[\phi]_{371}$ +7099.6°, $[\phi]_{366}$ +6905.1°, $[\phi]_{357}$ +8655.7°, $[\phi]_{348}$ +6321.6°, $[\phi]_{341}$ +7391.4°, $[\phi]_{335}$ +6127.1°, $[\phi]_{325}$ +11969.8°, $[\phi]_{316}$ +4638.3°, $[\phi]_{313}$ +4787.9°, $[\phi]_{310}$ 0, $[\phi]_{282}$ =43889.5°, $[\phi]_{260}$ −73415.2°, $[\phi]_{245}$ 0, $[\phi]_{231}$ +74200.8°, $[\phi]_{210}$ (last) 0; IR: $\nu_{max}^{CHCl_3}$ 1750 (cyclopentanone C=O), 1665 (conjugated ketone, 1600, 1585 (anisole) cm$^{-1}$; NMR: $\delta_{TMS}^{CDCl_3}$ 7.16 (multiplet, 1 proton, aromatic), 6.68 (multiplet, 3 protons, aromatic), 3.75 (singlet, 3 protons, –OCH$_3$), 1.18 (singlet, 3 protons, C$_{7a}$—CH$_3$) ppm.

Anal. Calcd. for C$_{19}$H$_{22}$O$_3$: C, 76.48; H, 7.43.
Found: C76.21; H, 7.47.

EXAMPLE 26

A solution of 0.8698 g. (2.92 mmoles) of the optically pure enedione from Example 25 in 15 ml. of ethanol 2B was stirred and cooled in an ice-salt bath to −8° while a solution of 30 mg. (0.793 mmole) of sodium borohydride in 25 ml. of ethanol 2B was added dropwise over a 15 minute period keeping the temperature below 0°. The reaction mixture was then stirred for 15 minutes at ~−3°. The pH was adjusted to 6-7 with 3N aqueous hydrochloric acid and after diluting with brine, the reaction mixture was extracted 3 times with ether. The ether extracts were combined, washed with brine, dried and filtered. Solvent removal gave a colorless oil which was chromatographed on silica gel (100 g.) to give 770.3 mg. (88.0%) of 1$\beta$-hydroxy-7,7a-dihydro-4[2-(3-methoxyphenyl)ethyl]-7aS-methyl-5(6H)-indanone as a pale yellow oil (eluted with 1:1 and 1:3 benzene:ether). IR: $\nu_{max}^{film}$ 3420 (OH), 1650 (conjugated ketone), 1600, 1585 (anisole) cm$^{-1}$. This material was essentially homogeneous on TLC analysis.

EXAMPLE 27

A 770 mg. (2.56 mmoles) sample of chromatographed ketol from Example 26 was hydrogenated in 30 ml. of absolute ethanol in the presence of 0.2 g. of Ak-4, 5% palladium on carbon (pre-equilibrated). After 2¼ hr., 66 ml. of hydrogen had been absorbed (64 ml. theory) and the hydrogenation appeared to have stopped. The catalyst was filtered, washed well with ethanol and the combined filtrate and washings were concentrated at reduced pressure to give a colorless oil. This material was chromatographed on 75 g. of silica gel affording 464 mg. (60.1%) of the saturated hydroxy ketone (mainly C/D-trans) as a colorless oil (eluted with 1:2 and 1:4 benzene:ether). IR: $\nu_{max}^{film}$ 3430 (OH), 1710 (cyclohexanone C=O), 1600, 1585 (anisole) cm$^{-1}$.

A solution of this material in 15 ml. of acetone was stirred in an ice-bath at 0° while 1.5 ml. of Jones reagent was added dropwise through a syringe. The reaction mixture was stirred for 5 minutes in the ice bath then the excess Jones reagent was decomposed with 2-propanol. The reaction mixture was poured into brine and extracted three times with ether. The ether extracts were combined, washed with brine, dried, and filtered. Solvent removal gave a pale yellow oil which was chromatographed on silica gel (50 g.) giving 434 mg. (93.8%) of the saturated diketone as a pale yellow oil (eluted with 4:1 and 1:1 benzene: ether); IR: $\nu_{max}^{film}$ 1740 (cyclopentanone C=O), 1715 (cyclohexanone C=O), 1600, 1585 (anisole) cm$^{-1}$.

A solution of this diketone in 10 ml. of methanol was stirred at room temperature while 2 ml. of 10N aqueous hydrochloric acid was added. The reaction mixture became warm and after 10 minutes, a white precipitate was present. After 4 hr. of stirring at room temperature, the reaction mixture was chilled in the refrigerator for 1½ hr. The white precipitate was filtered, washed with cold methanol and dried under vacuum to give 247.9 mg. of white solid, m.p. 130°–133°. Recrystallization from methanol gave 156.8 mg. (38.5%) of the pure d-(+)-3-methoxy-estra-1,3,5(10),9(11)-tetraen-17-one (9-dehydroestrone methyl ether) as white needle-like crystals, m.p. 142.5°–144°, homogeneous on TLC analysis; $[\alpha]_D^{25}$+290.92° (CHCl$_3$, C 0.5); IR: $\nu_{max}^{CHCl}$ 1735 (cyclopentanone C=O), 1605 (anisole) cm$^{-1}$; UV: $\lambda_{max}^{EtOH}$ 263 ($\epsilon$ 19300), 297 ($\epsilon$ 3400), $\lambda$infl$^{EtOH}$ 310 ($\lambda$ 2220) m$\mu$; ORD: (C 0.3034%, dioxane, 23°) $[\phi]_{700}$ +650.6°, $[\phi]_{589}$ +948.1°, $[\phi]_{321}$ +18812.4°, $[\phi]_{250}$ 0°, $[\phi]_{243}$ −1858.9°, $[\phi]_{240}$ 0°, $[\phi]_{226}$ +11153.6°, $[\phi]_{220/224}$ +8365.2°, $[\phi]_{216}$ 0°, $[\phi]_{210}$ (last) −9294.7°; NRM: $\delta_{TMS}^{CDCl_3}$ 7.52 (doublet, 1 armomatic proton), 6.68 (multiplet, 2 aromatic protons), 6.13 (multiplet, C$_{11}$—H,1 proton), 3.76 (singlet, OCH$_3$, 3 protons), 0.92 (singlet, C$_{13}$—CH$_3$, 3 protons) ppm. The IR, UV and NMR spectra were essentially identical to those of the known racemic form.

Anal. Calcd. for C$_{19}$H$_{22}$O$_2$: C, 80.81; H, 7.85.
Found: C, 80.53; H, 7.78.
Reported m.p. 142°–144°; $[\alpha]_D^{25}$ +289° (CHCl$_3$); $\lambda_{max}^{EtOH}$ 263 m$\mu$($\epsilon$ 17300).

EXAMPLE 28

A solution of 0.753 g. (2.54 mmoles) of diene prepared as in Example 7 in 5 ml. of ethanol and 2 ml. of benzene was stirred with cooling to −10°– −15° C. while 2.6 ml. (0.687 mmoles) of a 0.265 M ethanolic sodium borohydride solution was added dropwise over 5 minutes. The resulting mixture was stirred at −10°– +2° for 40 minutes then decomposed by acidification with 3N aqueous hydrochloric acid. After dilution with water and brine, the mixture was extracted three times with ether. The combined ether extracts were washed once with brine then dried, filtered and concentrated at reduced pressure affording a red oily residue. This material was chromatographed on 37.5 g. of silica gel giving 0.638 g. of pure (±)-1$\beta$-hydroxy-7,7a-dihydro-4-(m-methoxystyryl)-7a$\beta$-methyl-5(6H)indanone as an orange glass (eluted with 9:1, 4:1 and 1:1 benzene:ether).

ir: $\nu_{max}^{film}$ 3440 (OH), 1665 (conjugated ketone C=O), 1585, 1600 (anisole) cm$^{-1}$, uv: $\lambda_{max}^{EtOH}$ 221 m$\mu$ ($\epsilon$ 20400), 287 (16200).

EXAMPLE 29

A 0.617g. (2.07 mmoles) sample of diene ketol from Example 28 was hydrogenated in 25 ml. of ethanol over 0.3 g. of AK-4 5% palladium on carbon for 23 hours. The catalyst was filtered and the filtrate was concentrated at reduced pressure giving 0.597 g. of oily (±)-1$\beta$-hydroxy-3a,4,7,7a-tetrahydro-4[2-(3-methoxyphenyl)ethyl]-7a$\beta$-methyl-5(6H)indanone, which showed no $\mu$v absorbing spots on tlc nalysis. ir: $\nu_{max}^{film}$ 3380 (OH), 1710 (cyclohexanone C=O), 1590, 1600 (anisole)cm$^{-1}$.

EXAMPLE 30

The hydrogenation product from Example 29 was dissolved in 10 ml. of acetone and stirred with ice-bath cooling while 1 ml. of Jones reagent was added dropwise over 5 minutes. The resulting red mixture was stirred at 0°–5°for 5 minutes then decomposed with 2-propanol. After dilution with water and brine, the mixture was extracted three times with ether. The combined ether extracts were washed once with brine, dried, filtered and concentrated at reduced pressure giving 0.565 g. of yellow oil. Chromatography on 25 g. of silica gel gave 0.306 g. of (±)-3a,4,7,7a-tetrahydro-4[2-(3-methoxyphenyl)ethyl]-7a$\beta$-methyl-1,5(6H)indandione as a pale-yellow oil (eluted with 19:1 benzene:ether). ir: $\nu_{max}^{film}$ 1740 (cyclopentanone C=O), 1715 (cyclohexanone C=O), 1585, 1600 (anisole) cm$^{-1}$. The infrared spectrum was essentially identical to that of material produced previously in Example 9.

EXAMPLE 31

A mixture of 0.314 g. (1mmole) of alcohol as prepared in Example 6,0.460 g. (2 mmoles) of 4-bromobenzoyl chloride and 5 ml. of dry pyridine was stirred at room temperature for 5 hours. Water was then added and stirring was continued for several minutes. The mixture was acidified with dilute aqueous hydrochloric acid and extracted three times with ether. The combined ether extracts were washed once with water and twice with saturated aqeuous sodium bicarbonate solution then dried and concentrated at reduced pressure giving 0.597 g. of solid residue. This material was treated with methylene chloride and filtered to remove some insoluble material. This process was repeated on the filtrate and still a third time using benzene. The filtrate was concentrated and the residue was chromatographed on 25 g. of silica gel. The fractions eluted with 9:1 benzene: ether afforded 0.467 g. (94% of yellow crystalline (±)-7,7a-dihydro-4[2(3-methoxyphenyl)-2-(4-bromobenzolyloxy)ethyl]-7a$\beta$-methyl-1,5(6H)indandione p-bromobenzoate which was homogeneous on TLC analysis (R$_f$ 0.47). Recrystallization from ethanol gave 0.406 g. of pale-yellow solid, mp 139°–140°. Another recrystallization from ethanol gave the analytical specimen as pale-yellow crystals, mp 139°–140°; ir: $\nu_{max}^{CHCl_3}$ 1745 (cyclopentanone C=O), 1725 (aromatic ester C=O), 1670 ($\alpha,\beta$-unsaturated ketone C=O), 1590 (anisole) cm$^{-1}$; uv: $\lambda_{max}^{EtOH}$ 247 m$\mu$ ($\epsilon$ 29300);

nmr: $\delta_{TMS}^{CDCl_3}$ 7.72 (4 proton $A_2B_2$ multiplet, p-Br—C$_6$H$_4$—C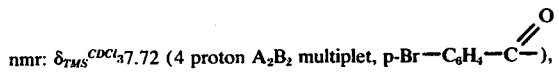—), 7.00 (4 proton multiplet, m—CH$_3$OC$_6$H$_4$—), 6.11 (triplet, J=7 Hz, H-C-O, 1 proton), 3.80 (singlet, CH$_3$O-, 3 protons), 1.13 (singlet, C$_{7a}$—CH$_3$, 3 protons) ppm; ms: m/e 496 (M$^+$).

Anal. Calcd. for C$_{26}$H$_{25}$BrO$_5$: C, 62.78; H, 5.07; Br, 16.06. Found: C, 63.04; H, 5.19; Br, 16.08.

EXAMPLE 32

A solution of 994 mg. (2 mmoles) of the bromobenzoate from Example 31 and 0.2 g. of p-tolenesulfonic acid monohydrate in 30 ml. of toluene was stirred and heated at reflux for 1½ hr. The reaction mixture was cooled, diluted with ether, washed with aqueous saturated sodium bicarbonate solution and brine, then dried and filtered. Solvent removal gave a yellow solid which was chromatographed on 60 g. of silica gel. Elution with 9:1 and 4:1 benzene:ether afforded 540.6 mg. (91.3%) of (±)-7,7a-dihydro-4-(m-methoxystyryl)-7aβ-methyl-1,5(6H)indandione as a yellow solid. Recrystallization of a sample from a similar experiment from ethanol-ether gave the analytical sample as a yellow solid, mp 93°—04°, which was homogeneous on TLC analysis (R$_f$ 0.47). UV: $\lambda_{max}^{EtOH}$ 220 ($\epsilon$ 21900), 279, ($\epsilon$ 15350), $\lambda_{sh}^{EtOH}$ 315 (11950) mμ; nmr: $\delta_{TMS}^{CDCl_3}$ 6.96 (multiplet, 6 protons, 4 aromatic, 2 vinyl), 3.79 (singlet, 3 protons, —OCH$_3$), 1.35 (singlet, 3 protons, C$_{7a}$—CH$_3$) ppm.

Anal. Calcd. for C$_{19}$H$_{20}$O$_3$: C, 77.00; H, 6.80. Found: C, 76.80; H, 6.69.

EXAMPLE 33

The crude diene obtained from 1.21 mmoles of pure bromobenzoate according to the procedure of Example 32 was hydrogenated in 20 ml. of dry toluene in the presence of 0.1 g. of AK-4, 5% palladium on carbon (pre-equilibrated). After 9 hours, 32.1 ml. of hydrogen had been absorbed (30.3 ml. theory) and the hydrogenation was stopped. The catalyst was filtered, washed with ether and the combined filtrate and washings were concentrated at reduced pressure to give a yellow oil (containing some solid) which was chromatographed on 35 g. of silica gel. Elution with 9:1 and 4:1 benzene-ether gave a yellow oil which was evaporatively distilled to give 317.6 mg. (87.6%) based on pure bromobenzoate of crude (±)-7,7a-dihydro-4-[2-(3-methoxyphenyl)ethyl]-7aβ-methyl-1,5(6H)indandione as a pale yellow oil, bp 160°-190° (bath)/0.03 mm. Ultraviolet analysis indicated some diene was still present. Upon rehydrogenating 261.4 mg. of this material in the above manner until the takeup of hydrogen appeared to have ceased (3.7 ml. of hydrogen had been absorbed in 1 hour) a colorless oil was obtained which was evaporatively distilled to give 249.2 mg. of the pure enedione as a yellow oil, bp 175°–190° (bath)/0.05 mm. TLC analysis showed one spot (R$_f$ 0.46). UV: $\lambda_{max}^{EtOH}$ 219 ($\epsilon$ 11200), 250 ($\epsilon$ 9400), 280 ($\epsilon$ 2750); nmr: $\epsilon_{TMS}^{CDCl_3}$ 7.14 (multiplet, 1 proton, aromatic), 6.66 (multiplet, 3 protons, aromatic), 3.73 (singlet, 3 protons, —OCH$_3$), 1.16 (singlet, 3 protons, C$_{7a}$—CH$_3$) ppm.

We claim

1. A process for the preparation of compounds of the formula

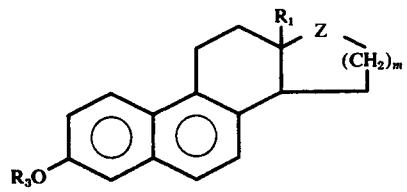

where
R$_1$ is a primary alkyl group of from 1 to 5 carbon atoms; R$_3$ is a cycloalkyl group, or a primary alkyl group from 1 to 8 carbon atoms; Z is carbonyl or a group of the formula

where R$_7$ is hydrogen, a group consisting of the residue of a hydrocarbyl monocarboxylic acid having from 1 to 18 carbon atoms formed by removal of the hydroxyl portion of the carboxyl group, lower alkyl, aryl lower alkyl or tetrahydropyran-2-yl and R$_8$ is hydrogen or lower aliphatic hydrocarbyl; and m is 1 or 2; which comprises reacting a compound of the formula

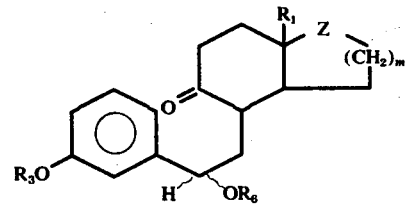

where
R$_1$, R$_3$, Z and m are as above; and R$_6$ is hydrogen, lower acyl or aroyl;
with a strong acid.

* * * * *

UNITED STATES PATENT AND TRADEMARK OFFICE
CERTIFICATE OF CORRECTION

PATENT NO. : 4,011,211
DATED : March 8, 1977
INVENTOR(S) : Noal Cohen and Gabriel Saucy It is certified that error appears in the above-identified patent and that said Letters Patent are hereby corrected as shown below:

Column 32, claim 1, lines 29-33

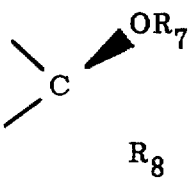

should be:

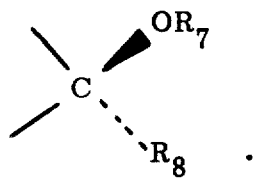

Signed and Sealed this

Thirteenth Day of November 1979

[SEAL]

Attest:

RUTH C. MASON
Attesting Officer

LUTRELLE F. PARKER
Acting Commissioner of Patents and Trademarks